(12) United States Patent
Kaltenberg et al.

(10) Patent No.: US 11,579,134 B2
(45) Date of Patent: Feb. 14, 2023

(54) SAMPLING FOR MONITORING PER- AND POLYFLUOROALKYL SUBSTANCES (PFAS) IN SURFACE WATER, GROUNDWATER AND PORE WATER

(71) Applicant: Battelle Memorial Institute, Columbus, OH (US)

(72) Inventors: Eliza M. Kaltenberg, Quincy, MA (US); Franco Pala, Rockland, MA (US); Kavitha Dasu, Hanover, MA (US); Fred Griesemer, Columbus, OH (US); Bradley Westlake, Columbus, OH (US); George Nanes, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 374 days.

(21) Appl. No.: 16/786,930

(22) Filed: Feb. 10, 2020

(65) Prior Publication Data

US 2020/0292516 A1    Sep. 17, 2020

Related U.S. Application Data

(60) Provisional application No. 62/900,109, filed on Sep. 13, 2019, provisional application No. 62/869,623, (Continued)

(51) Int. Cl.
*G01N 33/18* (2006.01)
*G01N 1/10* (2006.01)
(Continued)

(52) U.S. Cl.
CPC ........ *G01N 33/1826* (2013.01); *B01J 20/262* (2013.01); *B01J 20/2805* (2013.01);
(Continued)

(58) Field of Classification Search
CPC ...... G01N 33/1826; G01N 1/10; G01N 1/405; G01N 2001/1031; B01J 20/262;
(Continued)

(56) References Cited

U.S. PATENT DOCUMENTS 3,720,626 A    3/1973  Benzaria et al.
4,369,168 A    1/1983  Wells et al.
(Continued)

FOREIGN PATENT DOCUMENTS

CN    205749004 U   * 11/2016
FR      1409050 A      8/1965
WO    2013166406 A1   11/2013

OTHER PUBLICATIONS

Ahrens et al., (2011) "Partitioning of perfluorooctanoate (PFOA), perfluorooctane sulfonate (PFOS) and perfluorooctane sulfonamide (PFOSA) between water and sediment", Chemosphere 85(5): 731-737.
(Continued)

*Primary Examiner* — Christopher Adam Hixson
(74) *Attorney, Agent, or Firm* — Susanne A. Wilson; Frank Rosenberg

(57) ABSTRACT

Methods of passively sampling PFAS in the environment, PFAS sorbents, apparatus and systems (apparatus plus conditions) for sampling groundwater, porewater, and surface water are described.

10 Claims, 14 Drawing Sheets

Related U.S. Application Data filed on Jul. 2, 2019, provisional application No. 62/803,581, filed on Feb. 10, 2019.

(51) Int. Cl.

| | |
|---|---|
| *B01J 20/26* | (2006.01) |
| *B01J 20/28* | (2006.01) |
| *C08L 75/06* | (2006.01) |
| *C08L 75/08* | (2006.01) |
| *G01N 1/40* | (2006.01) |

(52) U.S. Cl.
CPC ......... *B01J 20/28045* (2013.01); *C08L 75/06* (2013.01); *C08L 75/08* (2013.01); *G01N 1/10* (2013.01); *G01N 1/405* (2013.01); *G01N 2001/1031* (2013.01)

(58) Field of Classification Search
CPC .............. B01J 20/28045; B01J 20/2805; B01J 20/265; B01J 20/28059; B01J 20/28069; B01J 20/28088; B01J 20/3285; C08L 75/06; C08L 75/08; C02F 2101/305; C02F 2101/36; C02F 103/007; C02F 103/06; C02F 2209/00; C02F 2303/16; C02F 1/285

See application file for complete search history.

(56) References Cited

U.S. PATENT DOCUMENTS

| | | | |
|---|---|---|---|
| 2017/0146435 A1 | 5/2017 | Smith | |
| 2017/0241870 A1 | 8/2017 | Smith | |
| 2019/0017983 A1 | 1/2019 | Smith | |
| 2019/0162638 A1* | 5/2019 | Shea | ........................ G01N 1/40 |

OTHER PUBLICATIONS

Gobelius et al., "Calibration and application of passive sampling for per- and polyfluoroalkyl substances in a drinking water treatment plant." Journal of Hazardous Materials, 2018, 362:230-237.
Hatton et al., "Occurrence and behavior of per- and polyfluoroalkyl substances from aqueous film-forming foam in groundwater systems," Remediation. 2018;28:89-99, Wiley Periodicals, Inc.
Stock et al., "Perfluoroalkyl contaminants in the Canadian Arctic: evidence of atmospheric transport and local contamination." (2007) Environ Sci Technol 41(10): 3529-3536.
Shoeib et al., (2006). "Perfluorinated chemicals in the arctic atmosphere." Environ Sci Technol 40(24): 7577-7583.
Kaserzon et al., (2012). "Development and calibration of a passive sampler for perfluorinated alkyl carboxylates and sulfonates in water." Environ Sci Technol 46(9): 4985-4993.
Kaserzon et al., (2019). "Calibration and validation of a novel passive sampling device for the time integrative monitoring of per- and polyfluoroalkyl substances (PFASs) and precursors in contaminated groundwater." Journal of Hazardous Materials 366: 423-431.
Place et al. (2012). "Identification of Novel Fluorochemicals in Aqueous FilmForming Foams Used by the US Military." Environmental Science & Technology 46(13): 7120-7127.
Vrana et al., (2005) "Passive sampling techniques for monitoring pollutants in water", Trends in Analytical Chemistry 24(10), 845-868. Elsevier Ltd.
Zhang et al., "Sorption of short- and long-chain perfluoroalkyl surfactants on sewage sludges", Journal of Hazardous Materials, 2013, vol. 260, pp. 689-699, Elsevier.
Xia et al., "Bioaccumulation of Perfluoroalkyl Substances by Daphnia magna in Water with Different Types and Concentrations of Protein", Environmental Science & Technology, 2013, vol. 47, No. 19, pp. 10955-10963.
Deng et al., "Selective sorption of perfluorooctane sulfonate on molecularly imprinted polymer adsorbents", Frontiers of Environmental Science & Engineering in China, vol. 3, No. 2, Jun. 1, 2009, pp. 171-177.
International Search Report and Written Opinion for International Application No. PCT/US2020/017564, dated May 27, 2020.
Machine translation of the description of French Patent No. FR1,409,050.
Ross et al., "A review of emerging technologies for remediation of PFASs", Remediation. 2018;28:101-126, Wiley Periodicals, Inc.
Bartlett et al., "Evaluating PFAS cross contamination issues", Remediation. 2018;28:53-57, Wiley Periodicals, Inc.
Liu et al., "Cost-Effective Reduced Graphene Oxide-Coated Polyurethane Sponge As a Highly Efficient and Reusable Oil-Absorbent", ACS Appl. Mater. Interfaces 2013, 5, 10018-10026, ACS Publications.
Dombrowski et al., "Technology review and evaluation of different chemical oxidation conditions on treatability of PFAS", Remediation. 2018;28:135-150, Wiley Periodicals, Inc.
Dixon-Anderson et al., "Field-Testing Polyethylene Passive Samplers for the Detection of Neutral Polyfluorinated Alkyl Substances in Air and Water", Environ Toxicol Chem 2018;99, SETAC.
Casson et al., "Integrating total oxidizable precursor assay data to evaluate fate and transport of PFASs", Remediation. 2018;28:71-87, Wiley Periodicals, Inc.
Anjaneyulu et al., "Removal and Recovery of Priority Pollutant Phenols from Industrial Effluents using Polyurethane Foam Medium", Oil & Chemical Pollution 1990, vol. 7, pp. 349-365, Elsevier Science Publishers Ltd, England.
Vedagiri et al., "Ambient levels of PFOS and PFOA in multiple environmental media", Remediation. 2018;28:9-51, Wiley Periodicals, Inc.
"Groundwater and PFAS: State of Knowledge and Practice; Remediation and Treatment", 2017, National Ground Water Association.
Yates, Brian J., "Per- and Polyfluoroalkyl Substances (PFAS) in Drinking Water; A PFAS Primer: Part I", Ohio Section AWWA Newsletter, Winter 2018, pp. 60-69.
"PFAS Assessment and Mitigation" pamphlet, 2017, Battelle Memorial Institute.
Darlington et al. "The Challenges of PFAS Remediation", The Military Engineer, Environmental Engineering Special Report: Innovative Technology Jan.-Feb. 2018, vol. 110, No. 712, SAME.
Liang et al., "Electrochemical oxidation of PFOA and PFOS in concentrated waste streams", Remediation. 2018;28:127-134, Wiley Periodicals, Inc.
"Remediation Technologies and Methods for Per- and Polyfluoroalkyl Substances (PFAS)" report, Mar. 2018, ITRC.
"Performance Fluorine Chemicals and Polymers", CHM024E Jan. 2017, BCC Research, Wellesley MA.
Impellitteri, Christopher, "Methods and Guidance for Sampling and Analyzing for PFAS in Environmental Media" webinar presentation, Nov. 28, 2018, EPA Office of Research and Development.
Vandermeyden, Carel, "Treatment Options for PFAS at a Surface Water Treatment Plant" presentation, Aug. 28, 2018, Cape Fear Public Utility Authority.
International Preliminary Report on Patentability in International Application No. PCT/US2020/017564, dated Aug. 10, 2021.

\* cited by examiner

SAMPLING FOR MONITORING PER- AND POLYFLUOROALKYL SUBSTANCES (PFAS) IN SURFACE WATER, GROUNDWATER AND PORE WATER

RELATED APPLICATIONS

This application claims the priority benefit of U.S. Provisional Patent Application Ser. Nos. 62/803,581; 62/868,123; and 62/900,109 filed 10 Feb. 2019, 2 Jul. 2019, and 13 Sep. 2019, respectively all of which are incorporated herein as if reproduced in full below.

INTRODUCTION

Per- and polyfluoroalkyl substances (PFAS) are a group of man-made chemicals which are potentially toxic and bioaccumulate in the bloodstream of most humans and animals throughout the world. PFAS has been shown to disrupt the normal endocrine activity, reduce immune function, accumulate in the liver, and have been shown to cause developmental problems in rodent offspring exposed in the womb. See Hatton et al., "Occurrence and behavior of per- and polyfluoroalkyl substances from aqueous film-forming foam in groundwater systems," Remediation, 2018; 28:89-99.

PFAS comprise a mixture of substances, most of which are anionic, but may also contain nonionic, zwitterionic, and cationic fluoroalkyl species. PFAS have unique chemical properties as being both hydrophobic and oleophobic and may form a separate phase in water or oil mixtures. The heat stability of PFAS and ability to block oxygen and suppress volatile vapors from flammable solvents have resulted in their common use as components of aqueous film-forming foams (AFFFs) (Place and Field 2012). PFAS are especially useful for fighting petroleum fires because the water repellency of PFAS is used to form a stable foam while the oil repellency prevents the foam from mixing with the petroleum, thus providing a foam that smothers the fire. See Hatton et al. cited above, who further remarked that "The ionic nature of the mobile, perfluorinated organic acids makes their behavior in an aqueous system complex and more difficult to predict than other organic contaminants. These differences from nonionic organic contaminants include interacting ionically with the aquifer matrix (soil, minerals, and rock), accumulating at various phase interfaces (such as air-water, oil-water, and oil air), and accumulating due to degradation of precursors." See Hatton et al. at page 96.

Due to their special properties, PFAS compounds have been utilized in a wide variety of commercial and industrial applications including: textiles, paints, packaging materials, non-stick products, and water-repellant clothing. PFAS detected in remote locations such as in arctic regions and is attributed due to the long range transport of some of the precursors such as fluorotelomer alcohols (FTOHs), perfluorinated sulfonamidoethanols (FOSEs), and sulfonamides (FOSAs), followed by the atmospheric transformation resulting in the deposition of persistent perfluorinated alkylacids in these regions (Ahrens et al. 2011, Stock et al. 2007, Shoeib et al. 2006).

Of particular concern, large quantities of PFAS have been used at military bases during training for extinguishing petroleum fires. As a result, ground water in the vicinity of these bases has been polluted with PFAS, and despite efforts to measure and clean up PFAS around these sites, there remains a substantial need for improved methods for measuring and remediating PFAS.

There have been numerous attempts reported in the literature to quantify PFAS in the environment. To detect neutral (non-ionic) PFAS in air and waste water effluent, Dixon-Anderson et al. tested various sampler materials. Low-density polyethylene sheets, 25 µm thick, were tested in passive sampling in air and wastewater effluent. The results were compared to active sampling using XAD (a crosslinked polystyrene copolymer resin conventionally used for adsorption of pollutants) sandwiched between 2 polyurethane foam plugs. The polyethylene sheets were submerged in the effluent outflow of a wastewater treatment plant or placed in air. The polyurethane foam plugs were tested in active sampling, either in wastewater effluent pumping at a rate of 20 L/day through the foam, or in through a pump-operated high-volume air sampler. Following exposure, the sampler materials were extracted with hexane. The extracts from the polyethylene sheets were analyzed to quantify a variety of PFAS species; however, Dixon-Anderson et al. reported that the extracts from the polyurethane foams used to sample water resulted in problems that prevented the quantification of PFAS species.

Kaserzon et al. (2019) proposed a passive sampler for PFAS consisting of an anion exchange sorbent (Strata X-AW) enclosed in a microporous polyethylene tube (Kaserzon et al. 2019). This sampler is a kinetic regimen sampler and required the analyte and site-specific sampling rates to be determined from in situ calibrations. Good agreement of sampling rates was observed for four out of five stations analyzed in this study; the reason for a different behavior of the passive sampler at one of the stations is unknown.

Polar organic chemical integrative samplers (POCIS) have been utilized for PFAS passive sampling to monitor anionic PFAS (Kaserzon et al. 2012; Gobelius et al (2018). Gobelius et al (2018) utilized a kinetic regiment passive sampler, which was calibrated in the laboratory and then tested on drinking water. The two POCIS configurations (two types of sorbent) were tested: POCIS—WAX (weak anion exchange) and POCIS-HLB (poly[divinylbenzene]-co-N-vinylpyrrolidone). Both the HLB and WAX adsorbent materials were assembled between two polyether sulfone (PES) membranes in passive samplers.

The motivation to develop an equilibrium regimen passive sampler instead of kinetic regimen is that the kinetic samplers are more difficult to use as the flow conditions of the sampled water can affect the uptake rates. The uptake curves (change of concentration of the analyte in the passive sampler with time) are typically linear for in the initial range where the uptake is constant, then the uptake starts slowing down until it finally ceases completely when the sorbate established equilibrium with the sorbent. Kinetic regimen passive samplers operate in the kinetic portion of the uptake and assume that the mass transfer to the sorbent is linearly proportional to the difference in chemical activities of the analyte in the receiving phase or the sorbent (Vrana et al., 2005). Calibration of the kinetic regimen passive samplers requires multiple time point samples to be collected, which then allows to calculate the sampler and analyte specific sampling rates. The sampling rates are often (for simplicity) derived in the laboratory experiments, even though field calibrations provide more relevant data. The sampling rates can vary significantly with site conditions (temperature, water flow energy, salinity, amount of biofouling formed on the sampler) and therefore laboratory derived calibrations often result in inaccuracies of the obtained results. An equilibrium regimen passive sampler, on the other hand, operates in the range where the concentration of the analyte in the sorbent reached a plateau and a thermodynamic equilibrium between the analyte in solution and the analyte in the passive sampler was achieved (Vrana et al., 2005). This equilibrium is described by the partition coefficient or distribution coefficient, which is not impacted by the site water energy or biofouling, eliminating the necessity for field calibrations. The partition coefficient value is slightly dependent on salinity and temperature of the sampled water, but the data can be easily corrected for these two factors during data processing.

Despite these and other efforts, there remains a need for improved methods for quantifying PFAS in the environment.

REFERENCES

Ahrens, L., L. W. Yeung, S. Taniyasu, P. K. Lam and N. Yamashita (2011). "Partitioning of perfluorooctanoate (PFOA), perfluorooctane sulfonate (PFOS) and perfluorooctane sulfonamide (PFOSA) between water and sediment." *Chemosphere* 85(5): 731-737.

Gobelius, L., C. Persson, K. Wiberg and L. Ahrens (2018). "Calibration and application of passive sampling for per- and polyfluoroalkyl substances in a drinking water treatment plant." *Journal of Hazardous Materials* 362: 230-237.

Kaserzon, S. L., K. Kennedy, D. W. Hawker, J. Thompson, S. Carter, A. C. Roach, K. Booij and J. F. Mueller (2012). "Development and calibration of a passive sampler for perfluorinated alkyl carboxylates and sulfonates in water." *Environ Sci Technol* 46(9): 4985-4993.

Kaserzon, S. L., S. Vijayasarathy, J. Braunig, L. Mueller, D. W. Hawker, K. V. Thomas and J. F. Mueller (2019). "Calibration and validation of a novel passive sampling device for the time integrative monitoring of per- and polyfluoroalkyl substances (PFASs) and precursors in contaminated groundwater." *Journal of Hazardous Materials* 366: 423-431.

Place, B. J. and J. A. Field (2012). "Identification of Novel Fluorochemicals in Aqueous Film-Forming Foams Used by the US Military." *Environmental Science & Technology* 46(13): 7120-7127.

Shoeib, M., T. Harner and P. Vlahos (2006). "Perfluorinated chemicals in the arctic atmosphere." *Environ Sci Technol* 40(24): 7577-7583.

Stock, N. L., V. I. Furdui, D. C. Muir and S. A. Mabury (2007). "Perfluoroalkyl contaminants in the Canadian Arctic: evidence of atmospheric transport and local contamination." *Environ Sci Technol* 41(10): 3529-3536.

Vrana, B., Mills, G. A., Allan, U., Dominiak, E., Svensson, K., Knutsson, J., Morrison, G., Greenwood, R. 2005. Trends in Analytical Chemistry 24(10), 845-868.

SUMMARY OF THE INVENTION

In one aspect, the invention provides a PFAS sorbent having hydrophilic and hydrophobic regions such that it exhibits a log $K_d$ of at least 2.5 or at least 3 for each of PFOA and PFOS and PFHxS; and a reversibility for PFHxA such that when exposed to a large volume of water (e.g., at least one liter of deionized water per 20 µg PFHxA for 3 weeks at STP) exhibits at least a 20% reduction of adsorbed PFHxA. $K_d$ values are determined as described herein. The water can be surface water, groundwater, or porewater. In some preferred embodiments, the PFAS sorbent has a log $K_d$ of at least 3 for each of PFOS and PFHxS; and/or the material has a log $K_d$ of 10 or less, or 7 or less, or 5 or less for each of PFOA and PFOS and PFBS. In some other embodiments, the upper limit of log $K_d$ may match that shown in Table 5. In some preferred embodiments, the PFAS sorbent exhibits a log $K_d$ of between 4 and 5 for each of NMeFOSAA and NEtFOSAA and/or a log $K_d$ of between 2.5 and 3 for each of PFHxA, PFHpA, PFOA, and PFNA. Preferably, the sorbent is a single material.

The PFAS sorbent has demanding requirements; preferably a single material (rather than a multitude of materials) is able to adsorb both relatively large (C12) and relatively small (C4) PFAS substances. The PFAS substances should also be extractable in solvents that do not destroy the sorbent so that the PFAS can be accurately measured (in this case desorbed according to the methods described herein). Furthermore, in order to accurately quantify a time-averaged level of PFAS (rather than the peak level of PFAS), it is desirable for at least a portion of the PFAS to desorb under conditions present in groundwater or surface water. In some preferred aspects, the PFAS sorbent is a polyurethane comprising carbamate and ester groups in the main chain, or comprising carbamate and ether groups in the main chain, with carbamate and ester groups in the main chain being especially preferred. It is believed that the best PFAS sorbents will have both hydrophilic and hydrophobic regions. However, this feature of the PFAS sorbent cannot be described based on composition; therefore, the measurements described herein must be used to define this feature.

The invention also includes methods of measuring PFAS in water. For example, a method of measuring PFAS, comprising: placing a sorbent in water for at least 24 hours, in some embodiments at least 5 days, in some embodiments at least 3 weeks, in some embodiments one to four weeks; removing the sorbent from the water; optionally removing excess water from the sorbent; extracting PFAS from the sorbent using a solvent that does not dissolve the sorbent; and analyzing the extracted PFAS for the amount of at least one component of PFAS.

For groundwater sampling, it has been found that, at least in some cases, it is important to limit the mass of sorbent in order to avoid PFAS depletion in the vicinity of the sorbent leading to inaccurate measurements. Thus, in another aspect, the invention provides a PFAS groundwater sampler, comprising: a housing comprising a wall or walls that define an internal cross-sectional area; a PFAS sorbent material disposed within the housing; wherein the sampler has a mass of at least 0.05 grams and a ratio of sorbent mass to housing internal cross-sectional area of no more than 3 g/10 cm², preferably no more than 1 g/10 cm². The internal cross-sectional area is defined as the area perpendicular to the central axis, where the central axis is the direction of gravity when the housing is disposed in a well.

Preferably, a PFAS sorbent is defined as a material having a log $K_d$ of at least 1.0 or at least 1.5 or at least 2.0 or at least 2.5 or at least 3.0 for each of PFOA and PFOS and PFBS; and a reversibility for PFHxA such that when exposed to a large volume of water (e.g., at least one liter of deionized water per 20 µg PFHxA for 3 weeks at standard temperature and pressure (STP)) exhibits at least a 20% reduction of adsorbed PFHxA. Log $K_d$ values are determined at standard conditions as set forth in the Examples section. Throughout this description, "log" means $Log_{10}$. The invention also includes a method of using the PFAS sampler to measure one or more components of PFAS in a well. Preferably, the well has a diameter of 20 cm or less, in some embodiments 10 cm or less, or 5 cm or less. Preferably, the sorbent is a polymer, optionally a polymeric foam. The invention also includes a method of measuring PFAS in groundwater comprising: placing the sampler of any of claims 6-7 down a well and into groundwater, allowing the sorbent to remain in the groundwater for at least 24 hours, removing the sorbent from the groundwater; optionally removing excess water from the sorbent; extracting PFAS from the sorbent using a solvent that does not dissolve the sorbent; and analyzing the extracted PFAS for the amount of at least one component of PFAS. At least one component of PFAS refers to any PFAS compounds; in some embodiments, it may be one or any combination of the 15 PFAS analytes reported in the Examples section.

In another further aspect, the invention provides a PFAS sampler, comprising: a PFAS sorbent film or foam that is covered by a copper mesh. In some embodiments, the PFAS sampler comprises five layers wherein the PFAS sorbent film or foam is sandwiched between two pieces of copper mesh and two pieces of stainless steel mesh such that the sampler comprises layers of the orders: stainless steel:copper:PFAS sorbent:copper:stainless steel.

In a further aspect, the invention provides sampling apparatus, comprising: housing comprising a plurality of compartments; wherein each compartment comprises a sorbent; and a mechanism that selectively opens or closes each compartment. In some aspects, the invention provides a passive sampler and a method of sampling comprising: exposing a first piece of sorbent to water at a selected site, closing off the first piece of sorbent, and, at a different time than the first sorbent is exposed, exposing a second piece of sorbent to water at the selected site. The time intervals are not identical and can overlap or not overlap; the second interval preferably starts later than the first. The sorbent is preferably selected to adsorb PFAS. The passive sampler is automated (typically containing an electronic timing device with actuator) and does not require a human to go to the site to extract and replace a sorbent. In some preferred embodiments, the passive sampler comprises mechanisms that expose the sorbent for a given time (e.g., three weeks), after which the first piece of sorbent is closed off, effectively capturing the past three weeks of site conditions. After another selected time period (e.g., the following three weeks), another piece of sorbent is closed off, etc. This can happen either through rotation of an external sleeve or through vertical movement of the sleeve (e.g. Rotary Shutter/Sleeve and Linear Shutter/Sleeve). In another set of preferred embodiments, after a desired period of time, sorbent is removed/separated the adjacent water, stopping the adsorption. This can be done through removing the sorbent piece from the water (External Winch/Lift or Buoyant Individual Segments) or through lowering an "air bell" into the well (Progressive Dive Bell Sleeve, Stationary Filled Dive Bell). Preferred designs are shown in the figures. The invention also includes methods of sampling using any of the apparatuses shown in the figures.

The invention also includes a method of measuring PFAS in groundwater comprising: placing the apparatus down a well and into groundwater, opening a first compartment while leaving a second compartment closed for at least 10 hours to expose a first sorbent to the groundwater, subsequently, opening a second compartment for at least 10 hours to expose a second sorbent to the groundwater, removing the first and second sorbents from the groundwater; optionally removing excess water from the sorbents; extracting PFAS from the sorbents using a solvent that does not dissolve the sorbent; and analyzing the extracted PFAS for the amount of at least one component of PFAS.

In a further aspect, the invention provides a PFAS sampler, comprising: an open-celled polymeric foam; and a vibrational motor adapted to vibrate the polymeric foam. The PFAS sampler may further comprise a metal (preferably stainless steel) screen disposed around the polymeric foam. In some embodiments, the PFAS sampler comprises a top flange and a bottom flange, rods disposed between the flanges, and the polymeric foam disposed on the rods or the polymeric foam enclosed in stainless-steel mesh screen casing and/or hinged-stainless steel frame, or the polymeric foam attached to an outside of a perforated core. The sampler can have a waterproof casing disposed on a top or bottom flange or in a rigid metal frame; wherein the waterproof casing comprises a compartment for batteries, and electrical circuitry adapted to connect the batteries to the vibrational motor; or a vibrational motor in a waterproof casing that is wired so that it can connect to an outside battery that can be placed above a water level. A hook can be attached to the top flange and adapted to hang the sampler in a hole. The invention also includes a method of measuring PFAS in surface water, porewater, or groundwater, comprising: placing the PFAS sampler of any of the above claims into the surface water, porewater, or groundwater; using the motor to vibrate the polymeric foam in the water; removing at least a portion of the polymeric foam from the water; and analyzing for PFAS that have been collected in the foam.

In another aspect, the invention provides a method of measuring PFAS in water, comprising: placing an open-celled polyurethane foam into the water; wherein the polyurethane comprises ether and/or ester moieties; removing at least a portion of the polyurethane foam from the water; and analyzing for PFAS that has been collected in the foam. The water can be porewater, surface water, or groundwater. The foam is preferably an ether or ester based polyurethane foam. In some embodiments, the foam comprises two types of polyurethane; preferably the two types are ether-polyurethane and ester-polyurethane. The method may further comprise measuring pH, DOC, temperature, and/or ionic strength of the water, and preferably using the measured pH, DOC and/or ionic strength to adjust at least one $K_d$ value and using the adjusted $K_d$ value to calculate the concentration of at least one PFAS compound.

The sorbent in any of the inventive aspects may preferably be an open-celled polymeric foam that is further characterizable by at least one or any combination of the parameters shown in Table 2, 4, or 5 and having a value of ±50% of that parameter as shown in Table 2, 4, or 5. The Langmuir-related values for 6:2 FTS, NMeFOSAA, NEtFOSAA, PFDS, PFUnA, and PFDoA are excluded from the characterization of the invention because the uncertainty in these values is too great.

In another aspect, the invention provides a method of measuring PFAS in water, comprising: placing an open-celled polymeric foam into the water; removing at least a portion of the polymeric foam from the water; and analyzing for PFAS that has been collected in the foam; and wherein the polymeric foam is characterizable by at least one of the parameters shown in Table 2, 4, or 5 and having a value of ±50% of that parameter as shown in Table 2, 4, or 5. The Langmuir-related values for 6:2 FTS, NMeFOSAA, NEtFOSAA, PFDS, PFUnA, and PFDoA are excluded from the characterization of the invention because the uncertainty in these values is too great. For example, the method may have a $C_e$ for PFOS of 411±50% µg/g sorbent (between 206 and 616 µg/g sorbent). $C_e$ is the concentration of PFOS in the sorbent at equilibrium.

In yet another aspect, the invention provides a method of measuring PFAS in water, comprising: placing an absorbent material, preferably an open-celled polyurethane foam, into the water; measuring pH, DOC and/or ionic strength of the water; removing at least a portion of the absorbent material from the water; and using the measured pH, DOC and/or ionic strength to adjust at least one $K_d$ value and using the adjusted $K_d$ value to calculate the concentration of at least one PFAS compound. In some embodiments, the ionic strength of the water is between 0.01 and 0.4 M or between 0.1 and 0.4 M. The method can include measuring the DOC of the water and using the measured DOC to adjust the $K_d$ value for PFDS and using the adjusted $K_d$ value to calculate the concentration of PFDS in the water. In general, the invention includes this method to measure any component of PFAS comprising measuring pH, DOC and/or ionic strength of the water.

We have found that polyurethane foams effectively sorb PFAS in aquatic samples. This is believed due, at least in part, to the interactions between the PFAS and the carbamate moieties in the polyurethane. Among the two types of polyurethane tested, we have found that the ether-based polyurethane is more effective in adsorbing most PFAS analytes, but ester-based polyurethane performed slightly better for the problematic short chain analytes which are more soluble and therefore harder to remove through sorption to passive samplers or water treatment substances such as granular activated carbon.

Polyurethanes have long been known as effective agents for extracting organic compounds. See, for example, Schumak et al. "Extraction of Aromatic Organic Compounds by Polyurethane Foam," Talanta, vol. 34, pp. 957-962 (1987); however, PFAS have unique properties that distinguish them from other organic compounds. As mentioned in the introduction, prior tests with polyurethane foams were unsuccessful, which prevented accurate quantification of PFAS from aqueous solutions. Surprisingly, we found polyurethane foams to be excellent materials for sampling PFAS from water. Also, surprisingly, we found ether-based polyurethane to exhibit substantially faster absorption of PFAS than ester-based polyurethane.

In order to sequestrate PFAS from dilute aqueous solution, the sorbent materials are selected according to their affinity to PFAS as well as their ultimate capacity for adsorption. Sorption depends on the existence affinity of a solid with molecules capable to reduce the potential energy of adsorbed molecule (PFAS) below that of the water. The forces of physical adsorption consist of the ubiquitous dispersion-repulsion forces (van der Waals forces), which are a fundamental property of all matter, supplemented by various electrostatic contributions (polarization, field-dipole and field gradient-quadrupole interactions of amine, amide, isocyanate groups interaction with carboxylic functional group), which can be important or even dominant for polar adsorbents. The nitrogen containing polymeric materials are expected to exhibit high affinity for carboxylic group presented in PFAS. For the PFAS passive sampler, the best results are obtained for material with high void space polyurethane in contrast to polyimide. Superior results are obtained for polyether urethane and polyester urethane; with polyester urethane especially preferred due to superior sorption reversibility.

Glossary porewater—water contained in pores of sediment or soil
groundwater—water held underground in the soil or in pores and crevices in rock; also referred to as GW in this document
surface water—water that collects on the surface of the ground (e.g., river, creek, lake, ocean); also referred to as SW in this document
kinetic regimen passive sampler—sampler operating in the uptake phase of sorption where the rate of mass transfer from water to the sorbent is proportional to the difference in chemical potentials of the analyte in the sorbent and sample
equilibrium regimen passive sampler—sampler operating in the equilibrium phase of sorption where the distribution of the analyte between sorbent and sample is described by the partition coefficient
passive sampler—sampler relying on spontaneous mass transfer of the analyte from sample to the sorbent caused by the difference in chemical potentials between the sample and sorbent
vibrational motor—a motor that creates vibrations, typically either through the use of unbalanced mass on a motor or through the used of internal mass attached to a spring
open-celled foam—reticulated foam; net-like foam with very few (if any) intact bubbles
Ester based polyurethane—polyurethane comprising ester linkages; also referred to as ester PUF and s-PUF in this document
Ether based polyurethane—polyurethane comprising ether linkages; also referred to as ether PUF and t-PUF in this document
Milli-Q water—ultrapure deionized water

ACRONYMS

μg—microgram
μm—micrometer
6:2 FTS—1H,1H,2H,2H-Perfluorooctane sulfonate
8:2 FTS—1H,1H,2H,2H-Perfluorodecane sulfonate
AFFF—aqueous film-forming foam
C—equilibrium aqueous concentration
C12—(PFAS) compound with 12 carbon atoms in the carbon chain
C4—(PFAS) compound with 4 carbon atoms in the carbon chain
Ce—equilibrium concentration of a given analyte in the sorbent
cm—centimeter
Cs—measured concentration of the analyte in the solid phase
Cw—measured aqueous concentration of the analyte
Cw-calc—water concentration calculated from on the passive sampler data
Cw-grab—average water concentration measured in grab water samples collected before deployment of the passive sampler and after retrieval of the passive sampler
DOC—dissolved organic carbon
FD—field duplicate
FOSA—perfluorinated sulfonamide
FOSE—perfluorinated sulfonamidoethanol
FTOH—fluorotelomer alcohol
g—gram
HDPE—high-density polyethylene
HLB—oly[divinylbenzene]-co-N-vinylpyrrolidone
HPLC—High Performance Liquid Chromatography
Hz—Hertz
k—kinetic rate constant
$K_d$—solid-water distribution (partition) coefficient
KF—Freundlich adsorption constant KF
kg—kilogram
KL—Langmuir adsorption equilibrium constant
L—liter
LC-MS/MS—liquid chromatography tandem mass spectrometry
log—logarithm to the base 10

M—molar
MEA—monoethylamine
mL—milliliter
mm—millimeter
mM—millimolar
n—Freundlich adsorption constant n
NaCl—sodium chloride
NaOH—sodium hydroxide
N-EtFOSAA—N-ethylperfluoro-1-octanesulfonamido-acetic acid
ng—nanogram
N-MeFOSAA—N-methylperfluoro-1-octanesulfonamido-acetic acid
PES—polyether sulfone
PFAS—per- and polyfluoroalkyl substances
PFBA—perfluoro-n-butanoic acid
PFBS—perflurorbutanesulfonic acid
PFDA—perfluorodecanoic acid
PFDoA—perfluorododecanoic acid
PFDS—perfluoro-1-decanesulfonate
PFHpA—perfluoroheptanoic acid
PFHxA—perfluororhexanoic acid
PFHxS—perfluoro-1-hexanesulfonate
PFNA—perfluorononanoic acid
PFOA—perfluorooctanoic acid
PFOS—perfluorooctanesulfonic acid
PFUnA—perfluoroundecanoic acid
POCIS—polar organic chemical integrative sampler
PP—polypropylene
PPI—pores per inch
PRC—performance reference compound
PUF—polyurethane foam
q—equilibrium amount of analyte on the sorbent
qmax—sorption capacity
R2—coefficient of determination
SPE—solid phase extraction
STP—standard temperature and pressure
Strata X-AW—weak anion exchange resin by Phenomenex®
t—time
TOC—total organic carbon
v/v—volume by volume
$V_0$—initial sorption rate
WAX—weak onion exchange resin
XAD—ion exchange resin produced by Amberlite™

DETAILED DESCRIPTION OF THE INVENTION

Sorbent

Figure 1:
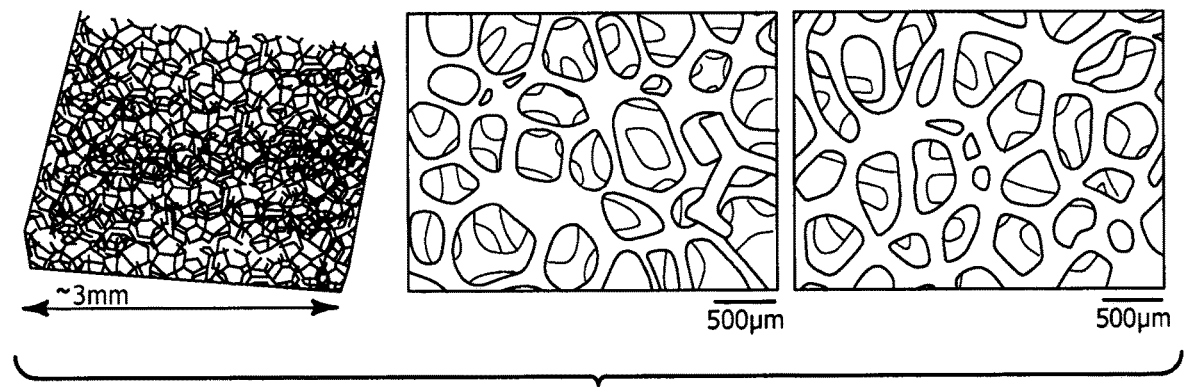
FIG. 1. Reticulated polyurethane foam. Visual appearance with a naked eye is presented on the left. The middle panel is the microscopic image of ether-PUF, and the right panel is the microscopic image of ester-PUF, with both scale bars showing 500 µm.

Polymers containing carbamate (urethane groups) groups in the main chain are preferred, even more preferred are polymers containing carbamate and ether groups or carbamate and ester groups in the main chain. In a related aspect, the invention includes an open-celled polymer foam comprising PFAS and water, where the polymer containing carbamate and ether groups or carbamate and ester groups in the main chain. We have found that polyurethane foams effectively sorb PFAS in aquatic samples. This is believed due, at least in part, to the interactions between the PFAS and the non-carbon atoms that are part of the polymer main chain. Among polymers tested, we have found that polymers containing both carbamate and ether groups in the main chain are more effective in adsorbing most PFAS analytes, but polymers containing both carbamate and ester groups in the main chain performed slightly better for the problematic short chain analytes which are more soluble and therefore harder to remove through sorption to passive samplers or water treatment substances such as granular activated carbon.

Foam

In some preferred aspects, the invention may use a polymeric, open-celled foam to adsorb PFAS in a passive sampler, and a rigid holder allowing direct placement in the sampled water and an optional transfer of vibrations from a vibrational motor. The preferred sorbent material is polyurethane, especially an open-celled polyurethane foam in which the an organic carbamate moiety [—NH—(C=O)—O—] linked through an ether or ester linkage. The adsorptive phase is a solid that, due to its surface properties, interacts with PFAS and concentrates them on the solid surface. The polymeric sorbent material (or combination of materials) is suitable for both ionic and neutral PFAS.

The foam preferably has an open pore structure having 200 or less pores per inch (measured linearly along a cross-section), preferably 10-150 or 45 to 100 pores per inch which allows free flow of water though the material. Higher density (more pores per inch) material could be used to increase the surface area of the sampler when needed. Higher surface area would be beneficial for sites with low concentrations of the analytes because it allows to collect more analytes and therefore increase the detection limits. It could be also beneficial at sites where due to the space restrictions that overall dimensions of the passive sampler must be minimized (e.g., in small internal diameter groundwater monitoring wells. The foam material is typically deployed in sheets of material, for example a sheet in the range of 0.1 to 1 inch thick, or 0.1 to 0.5 inch thick, or 0.25 to 1 inch thick.

The foam may alternatively, or in addition, be described by other characteristics. For example, the foam may alternatively, or in addition, be described by its partition coefficient as measured under specified conditions. Other material characteristics of the foam include specific surface area, porosity, acidity and basicity of the material surface, size of the micropores, and zeta potential (a measure of the surface charge).

In the examples section, testing of two types of polyurethane foam are described: an ether-based polyurethane and an ester-based polyurethane. Both types of polyurethane foam (PUF) were obtained from UFP Technologies (see FIG. 1). One PUF was ester-based and the other one was ether-based. Both were in the form of 0.25-inch-thick sheets with opening size of 45 pores per inch (PPI) which allows for unrestricted flow of water through the pore space. Both PUFs were dark grey/black in color, with ether-PUF being darker, almost black, and ester-PUF being dark grey color. Surface area of both materials was determined using BET method and was determined to be 0.5293 $m^2/g$ for ether-PUF and 0.3837 $m^2/g$ for ester-PUF. The total pore volume of pores less than 24.6 Å in size determined form single point adsorption was 0.000215 $cm^3/g$ for ether-PUF. For ester-PUF, the total pore volume of the pores less than 24.6 Å in size was 0.000154 $cm^3/g$. That means that the ether-PUF is approximately 40% higher both in the surface area and the total volume of micropores compared to ester-PUF. In some preferred embodiments, the surface area of the foam, as measured by BET, is at least 0.40 $m^2/g$, preferably at least 0.50 $m^2/g$, in some embodiments in the range of 0.35 to 0.70 $m^2/g$, 0.40 to 0.60 $m^2/g$, or 0.45 to 0.35 $m^2/g$. In some preferred embodiments, the total pore volume of pores less than 25 is preferably at least 0.00018 $cm^3/g$, or at least 0.00020 $cm^3/g$, in some embodiments in the range of 0.00015 to 00030 $cm^3/g$, or 0.0020 to 0.0025 $cm^3/g$.

Prior to use, the foams were cleaned by soaking in methanol three times to remove any contaminants. The volume of methanol used in this step is not critical as it has very high affinity for PFAS and other contaminants, but it is advised to provide enough volume of methanol to allow the foam to move freely during agitation. Up to 5 grams of foam would be appropriate for 250 milliliters of methanol.

An ether-based polyurethane comprises carbamate groups bonded through molecular chains comprising ether moieties. The ether-based polyurethane has a ratio of ether moieties to carbamate moieties of at least one, typically at least 5, preferably at least 10, in some embodiments 2 to 20 or 2 to 10; preferably, carbamate moieties are connected through polyether linkages. Likewise, an ester-based polyurethane comprises carbamate groups bonded through molecular chains comprising ester moieties. The ester-based polyurethane has a ratio of ester moieties to carbamate moieties of at least one, typically at least 5, preferably at least 10, in some embodiments 2 to 20 or 2 to 10; preferably, carbamate moieties are connected through polyester linkages.

Housing/Supports

The housing and/or support for the polymeric foam may be varied depending upon the application site. For example, the polymeric foam may be framed in hinged stainless-steel frames, inserted into a stainless-steel mesh sleeve, or attached to a perforated core. The invention includes devices and methods in which an anti-biofouling screen is placed over (in some embodiments, in direct contact with) a PFAS adsorbent. In preferred embodiments, a polymeric foam adsorbent is sandwiched between anti-biofouling screens. In some embodiments, the anti-biofouling screen is placed directly in contact with the adsorbent, in other embodiments, one or more porous inert layers can be disposed between the adsorbent and the anti-biofouling screen.

Figure 2:
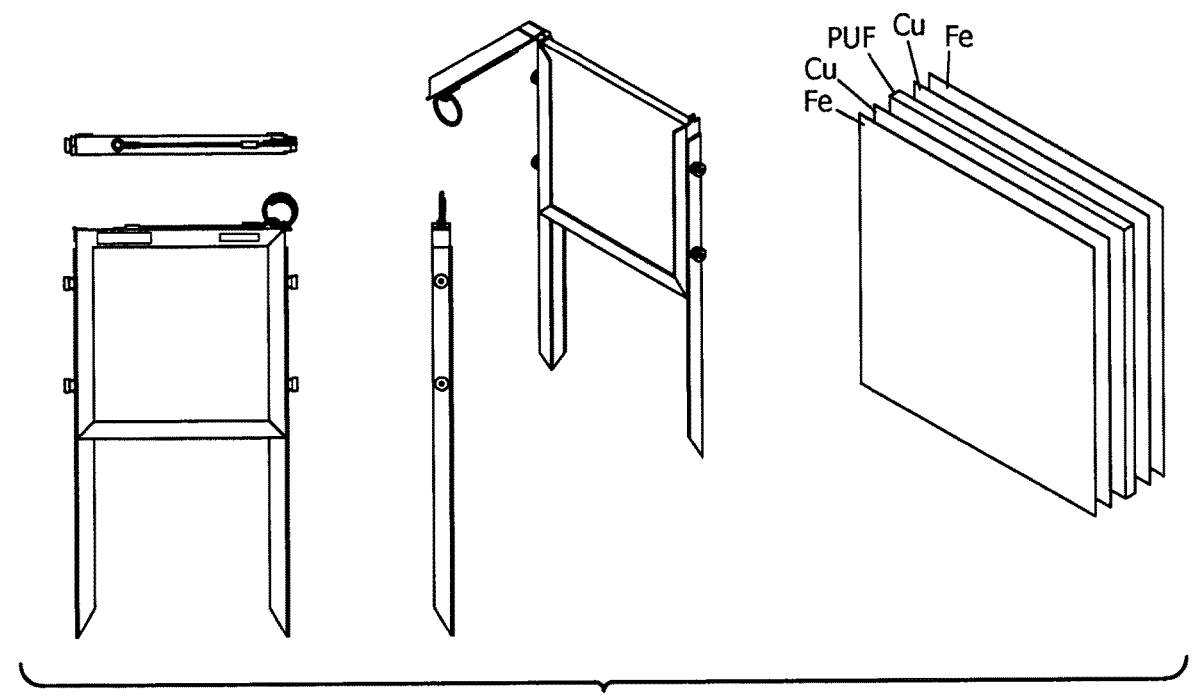
FIG. 2 illustrates a structure of a passive sampler suitable for use in surface water.
Figure 3:
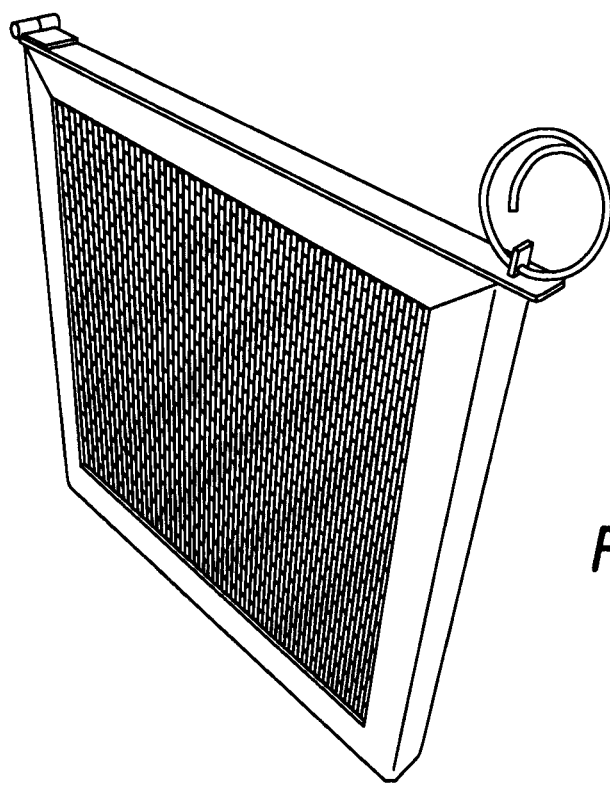
FIG. 3 is a photograph of an assembled passive sampler.

A preferred construction for surface water deployment is illustrated in FIG. 2. The porous polymeric foam adsorbent is sandwiched between copper screens that are, in turn, sandwiched between stainless steel screens, and the laminate is housed in a stainless steel frame. The copper screen is preferably of a fine mesh (for example, a mesh size 200 per inch, opening size of, for example, 0.003 inch, opening percent, for example, of 35%) and provides protection from particulates and biofouling through its growth inhibiting properties. Stainless steel mesh is much coarser (e.g., ⅛-1/16 inch) and provides structural stability to the design. The top part of the frame is hinged allowing opening and closing of the frame, which is held together by a ring. Finally, two "legs" are attached to the frame on both sides. The legs provide the insertion part of the frame, in this scenario designed for shallow surface water where the legs are to be inserted into the sediment. Other mounting features (suspension loops, triangular drive point, screws allowing attachment to existing underwater structures or buoys) could be used as well.

Figure 4:
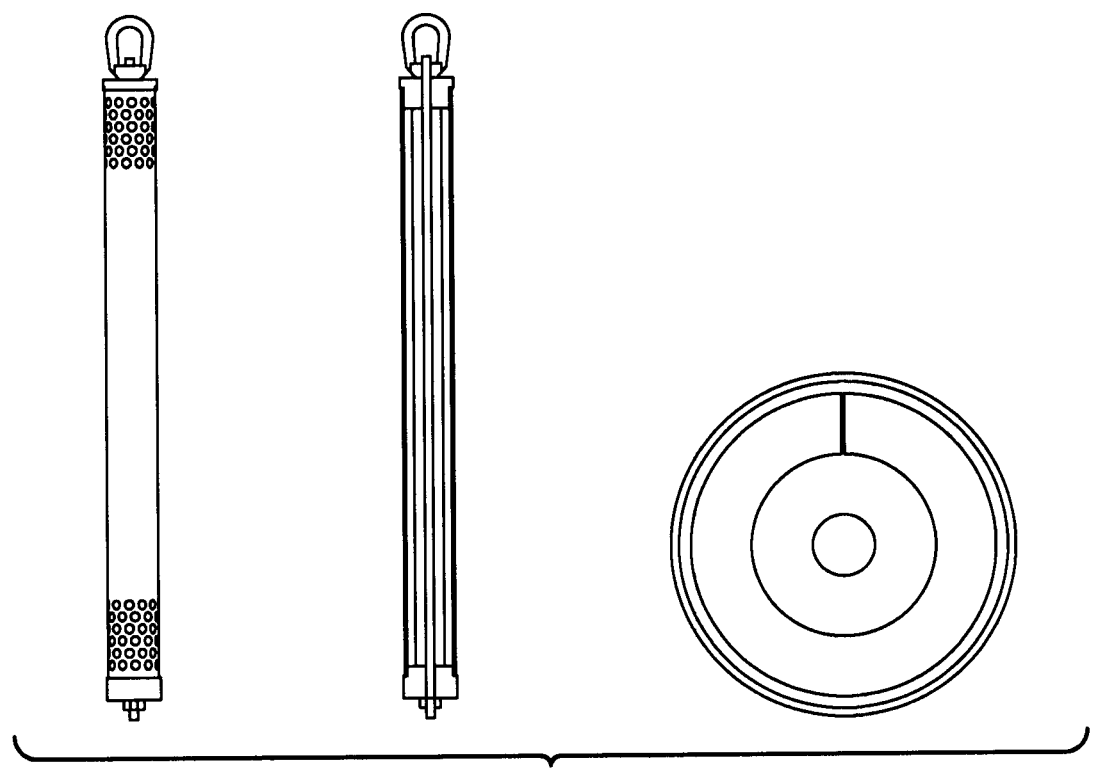
FIG. 4 illustrates a structure of a passive sampler suitable for use in ground water. Shown, from left to right is a side view, cross-sectional side view, and cross-sectional overhead view.
Figure 5:
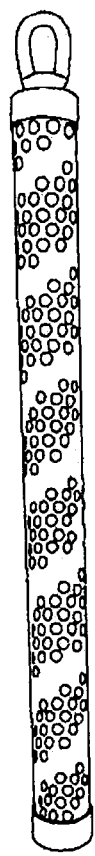
FIG. 5 is a photograph of a ground water sampler.

A device for sampling in a groundwater well is illustrated in FIG. 4. In the illustrated design, a porous polymeric foam adsorbent is disposed between an inner support rod and an outer cylinder and the cylinder is capped on both ends with threaded caps, and the top cap is equipped with a loop. Perforations in the outer cylinder allow the flow of water through the foam. Note that in the attached picture, perforation holes are only drawn in the top and bottom of the design; however, in some preferred embodiments, perforations extend for the entire length of the design. The whole apparatus is suspended by a cable attached to the loop located in the top of the apparatus.

The invention also provides apparatus and methods of acquiring analyte samples that are designed to collect a plurality of samples over a plurality of selected time intervals. A single passive sampler can be placed in a site of PFAS-contaminated water and adsorb PFAS over any selected time period, and a single device can collect multiple samples, each of which is collected over a different, selected time period. To do that, multiple pieces of sorbent (a preferred sorbent is a polymeric foam) are placed inside the hardware, which is equipped with separated compartments for each piece of sorbent and a mechanism that exposes each piece of sorbent one after another. This can be achieved through a variety of mechanisms schematically drawn below. The modes of operation can be generally divided into two groups. The first group are mechanisms that exposed the sorbent for a given time (e.g., three weeks), after which the first piece of sorbent is closed off, effectively capturing the past three weeks of site conditions. After another three weeks, another piece of sorbent is closed off, etc. This can happen either through rotation of the external sleeve or through vertical movement of the sleeve (e.g. Rotary Shutter/Sleeve and Linear Shutter/Sleeve). The second group of methods are methods that after the desired period of time remove/separate the sorbent from the adjacent water, stopping the adsorption. This can be done through removing the sorbent from water (External Winch/Lift or Buoyant Individual Segments) or through lowering an "air bell" into the well (Progressive Dive Bell Sleeve, Stationary Filled Dive Bell).

Figure 6:
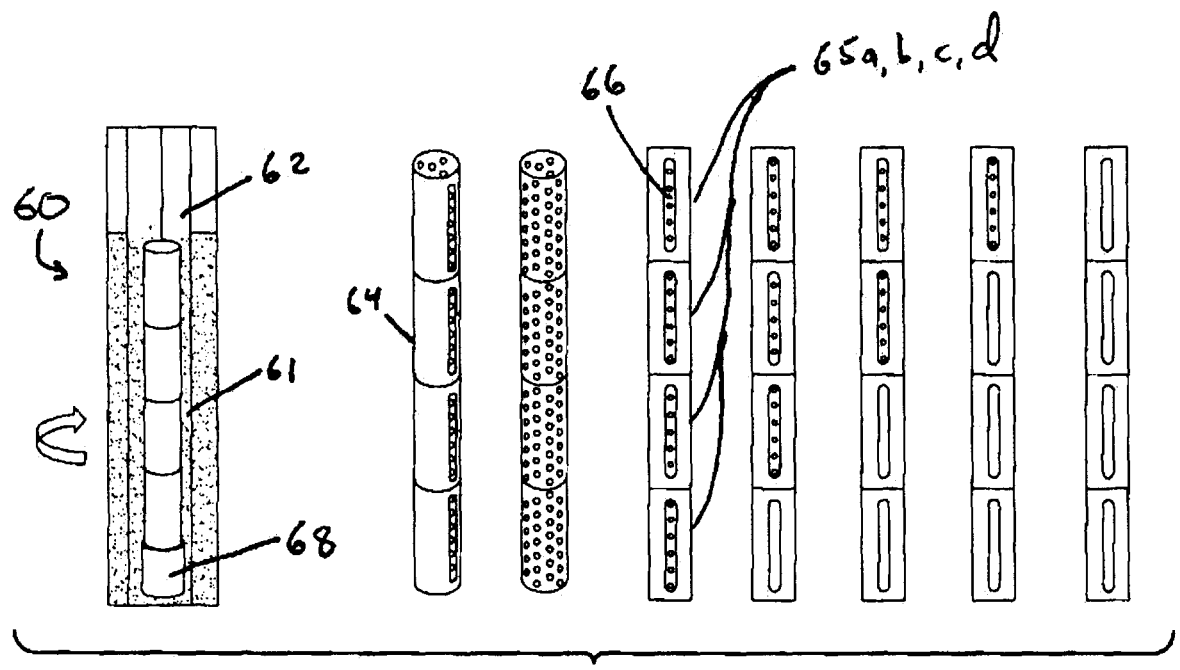
FIG. 6 illustrates a rotary shutter/sleeve passive sampler device.

FIG. 6 illustrates a rotary shutter/sleeve device 60 disposed in groundwater 61 within a well 62 in which a sleeve 64 can be turned to expose separate compartments 65a,b,c,d, and if desired close selected compartments, to collect data over selected time intervals. Each compartment comprises an adsorbent 66. The compartments are powered to be opened and/or closed by rotary actuator 68 that is attached to the device. The separate rotations of each compartment are shown in the figure.

Figure 7:
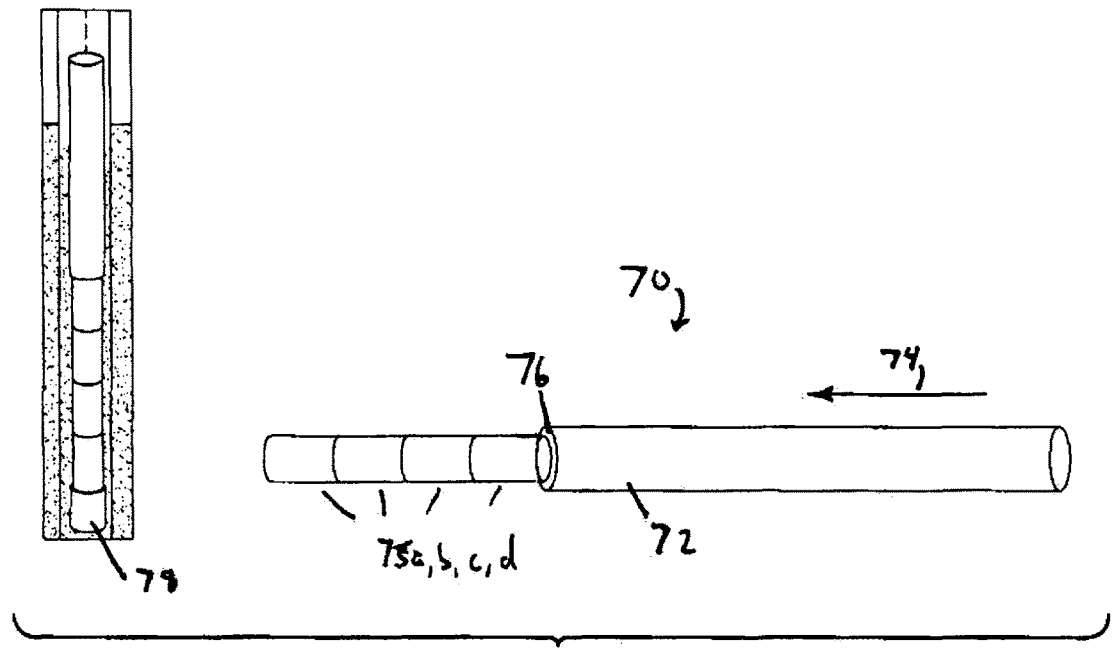
FIG. 7 illustrates a passive sampler with a movable sleeve for sequentially exposing or sealing compartments enclosing a sorbent material.

FIG. 7 illustrates a passive sampler 70 with a sleeve 72. The sleeve can be used either (or both) to sequentially expose compartments as the sleeve is lifted over time. Alternatively, or in addition, the sleeve can be slid down 74 over the compartments 65a,b,c,d, to sequentially seal compartments. The sleeve can include seal 76 Actuator 78 powers the sleeve.

Figure 8:
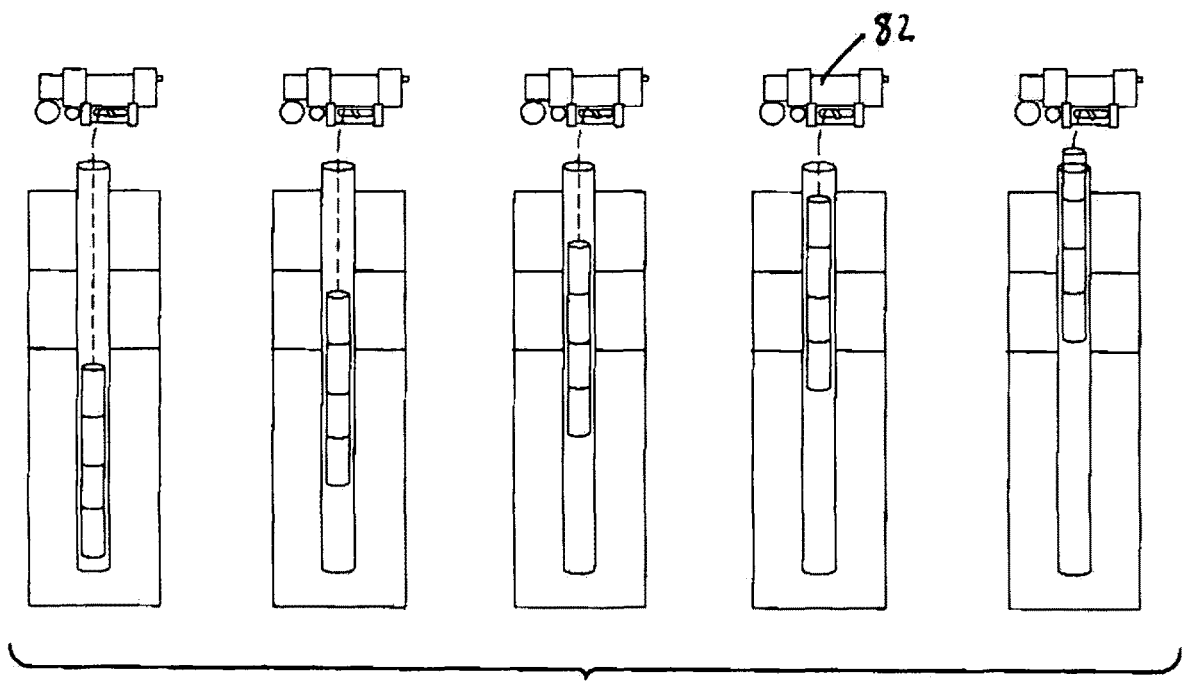
FIG. 8 illustrates a passive sampler comprising a plurality of compartments attached to a winch.

FIG. 8 illustrates a passive sampler comprising a plurality of compartments. A winch 82 is attached to the sampler that can move the sampler either up or down to remove or expose compartments to the water to be sampled.

Figure 9:
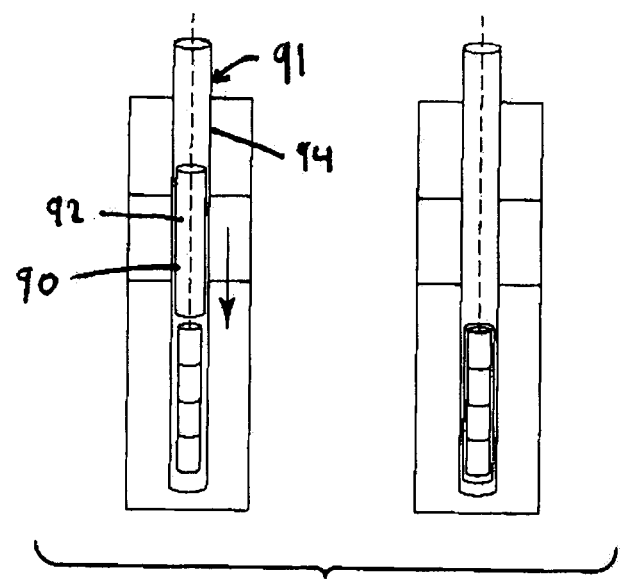
FIG. 9 illustrates a passive sampler comprising a plurality of compartments attached to a diving bell.
Figure 10:
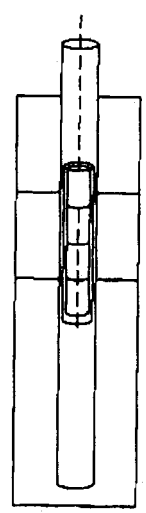
FIG. 10 is similar to FIG. 9 except that the sampler begins with diving bell pulled over the compartments and air can be pumped into the bell to sequentially remove water to be sampled as the bell fills with air.

FIG. 9 illustrates a passive sampler 91 comprising a plurality of compartments. As in the other examples, each compartment contains a separate sorbent. A dive bell 90 comprising air 92 passes over the compartments to sequentially replace the water with a gas (typically air) to sequentially remove the sorbent from the water being sampled. The compartments and dive bell are housed within a screen 94. FIG. 10 operates in a similar fashion except the bell remains stationary while gas is pumped into the bell to sequentially remove water from sorbent compartments as the bell fills with gas.

Figure 11:
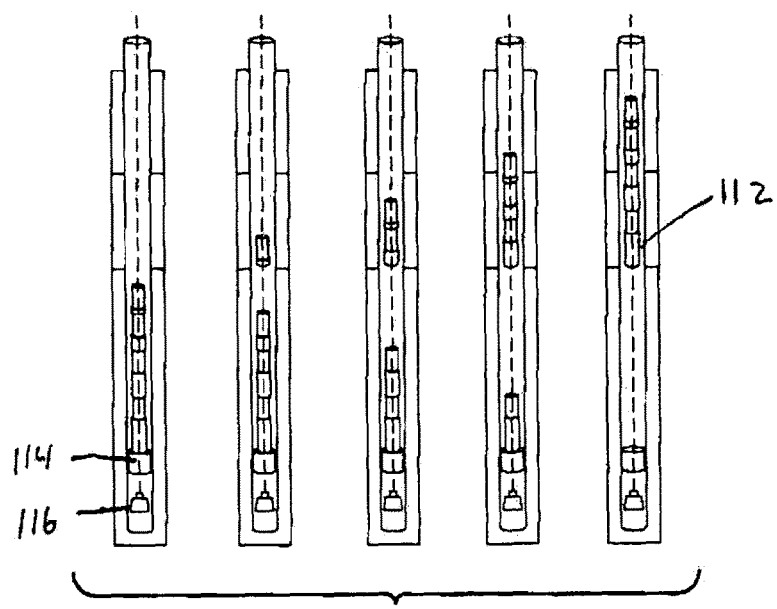
FIG. 11 illustrates a passive sampler having individual buoyant segments.

FIG. 11 illustrates a passive sampler comprising a plurality of buoyant sorbent compartments 112 each comprising a sorbent. A counterweight 116 keeps the buoyant compartments submerged. An actuator 114 releases selected compartments to provide a time-release of selected compartments.

Figure 12:
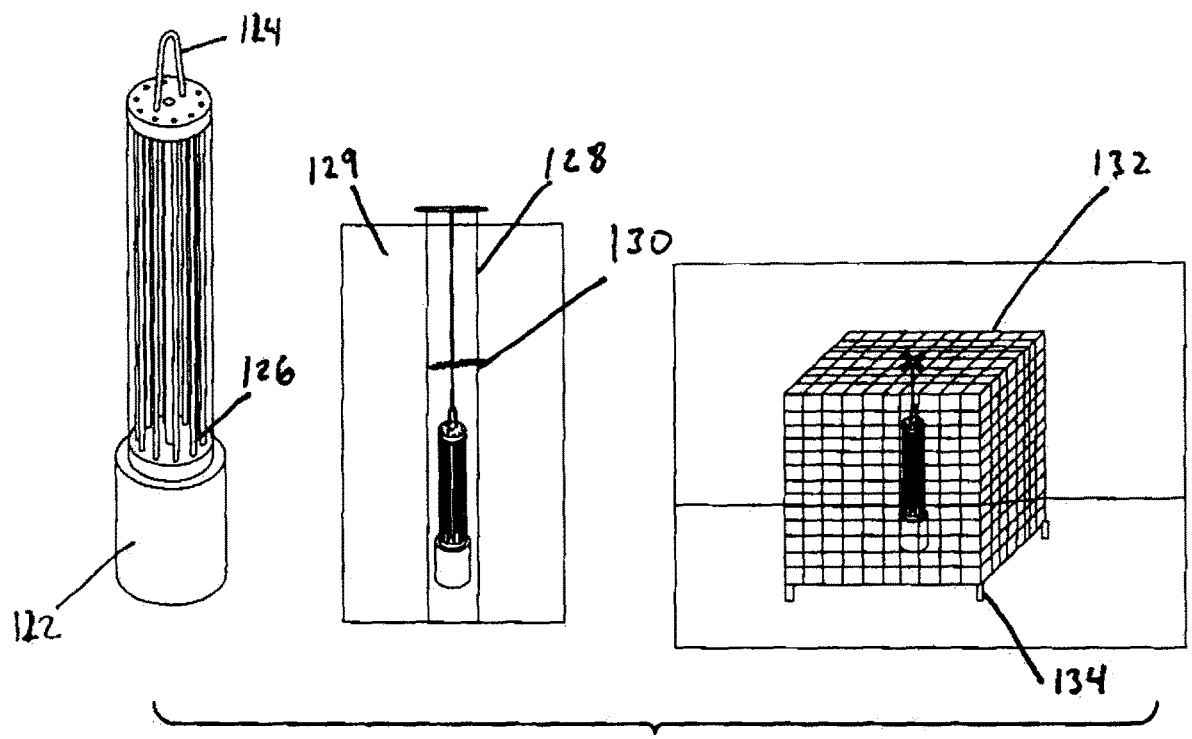
FIG. 12 illustrates deployment of a passive sampler having an attached vibratory motor.

FIG. 12 illustrates deployment of a passive sampler having an attached vibratory motor 122. A loop 124 permits the sampler to hang from a hook above the well drilled into the ground 129. A sorbent material can be wrapped around rods 126. The passive sampler can be hung in a well 128 below water level 130. The vibrations provide enhanced diffusion of PFAS compounds to the sorbent. A vibratory motor can be attached to any of the samplers to enhance diffusion. The drawing at the far right of FIG. 12 shows the passive sampler hung from a large mesh cage 132. Feet 134 can be added for stability.

In some aspects, the invention provides a passive sampler and a method of sampling comprising: exposing a first piece of sorbent to water at a selected site, closing off the first piece of sorbent, and, at a different time than the first sorbent is exposed, exposing a second piece of sorbent to water at the selected site. The time intervals are not identical and can overlap or not overlap; the second interval preferably starts later than the first. The sorbent is preferably selected to adsorb PFAS. The passive sampler can be automated (typically containing an electronic timing device with actuator) and does not require a human to go to the site to extract and replace a sorbent. In some preferred embodiments, the passive sampler comprises mechanisms that expose the sorbent for a given time (e.g., three weeks), after which the first piece of sorbent is closed off, effectively capturing the past three weeks of site conditions. After another selected time period (e.g., the following three weeks), another piece of sorbent is closed off, etc. This can happen either through rotation of an external sleeve or through vertical movement of the sleeve (e.g. Rotary Shutter/Sleeve and Linear Shutter/Sleeve). In another set of preferred embodiments, after a desired period of time, sorbent is removed/separated the adjacent water, stopping the adsorption. This can be done through removing the sorbent piece from the water (External Winch/Lift or Buoyant Individual Segments) or through lowering an "air bell" into the well (Progressive Dive Bell Sleeve, Stationary Filled Dive Bell). The invention includes any of the passive samplers illustrated in the figures.

The size of the passive sampler can be customized to the site conditions. For surface water deployments, passive sampler can be protected from the particulates with a fine-mesh stainless steel, to protect the sorbent from suspended particulates. Stainless-steel mesh screens with the nominal size ("nominal" meaning the size of particles that can pass through the openings) of 2-100 micrometers are preferred because smaller size mesh may necessitate longer exposure times. The stainless steel provides protection from particulate contamination and physical damage to the sampler during exposure but does not suffer from the same problems typical membranes would cause for PFAS which is adsorption of PFAS to the membrane itself. The sorbent may be also protected from growth of biofouling with a fine-mesh copper screen. The passive sampler can be suspended from a surface buoy or anchored above the sediment. For groundwater, a narrow passive sampler holder will be used such that the sampler fits freely inside the well without restricting the flow. The passive sampler will be lowered into the well using a PFAS-free cable, preferably the cable is stainless steel although polymer (e.g., Nylon) cable may be used if depletion of PFAS within the well is not an issue. The cable can be attached to the outside of the well to hold the passive sampler within the screened interval of the well. The passive sampler will be deployed for a period of time, in some embodiments 2-8 weeks or 2-4 weeks, after which it will be retrieved.

Motor/Vibrator

The sorbent may be connected to a vibrational motor (FIG. 12). The vibration reduces the thickness of the depletion layer at the foam-water interface, thereby increasing the mass transport of PFASs molecules and reducing the equilibration time needed for the monitoring of PFAS in aquatic systems. The motor placed in a waterproof casing which is attached to one side of the frame/casing. The frame/casing is made of a rigid material providing excellent transmission of the vibrations, regardless of partial damping of the vibration by the polyurethane itself. The vibrational motor is equipped with a timer allowing application of energy-saving periodic vibrations that can be adjusted for optimum performance. The motor is powered by a battery that can be placed in a waterproof casing and submerged (e.g. in surface water) or left on the ground surface and connected to the motor with a wire (e.g. for groundwater monitoring well). The motor would provide a minimum 1 Hz vibration, preferably at least 50 Hz, or a range of 1 to 500 Hz, 50 to 400 Hz, or 100-200 hertz vibration frequency with the resulting oscillation amplitude of at least about 1 millimeter, or in the range of 1 to 5 mm, or 1 to 3 mm.

Methods of Collection

Preparation:

Prior to deployment, the polymer is cleaned to remove any potential unpolymerized compounds or other contaminants that could interfere with PFAS measurements. This also provides a confidence that no new contaminants will be introduced into the sampled water via passive sampler deployment. Performance reference compounds (PRCs) are sometimes added to other types of passive samplers before deployment to determine if equilibrium was achieved, and if necessary, correct the data for lack of equilibration. Because the PFAS passive sampler was shown to achieve equilibrium in days to weeks (depending on the analyte), the use of PRCs may not be required. However, PRCs could be used in limited flow conditions such as low-permeability porewater where prolonged equilibration times are expected. If PRC use is deemed necessary, polyurethane material can be cleaned as described above, then immersed in an aqueous solution of PRC compounds which display similar properties to the analytes but are absent from the sampling environment. The passive sampler will comprise the polymer adsorbent (optionally spiked with PRCs), stainless-steel parts (frame/canister/mesh), and potentially a laboratory grade membrane, preferably a stainless steel membrane, and an optional copper mesh serving as an anti-biofouling agent.

Deployment:

Generally, from one to any number of samplers can be employed at a site, for example, 3 to 10 samplers. The number may vary, depending on the specific project goals, expected site variability, desired type one and type two errors, and the project budget. Passive sampler should be deployed in so that it is always submerged, which will be of particular concern when sampling near intertidal areas.

For surface water, the sampler can be anchored above the sediment or suspended from a buoy or a permanent underwater structure (e.g. a dock).

For porewater sampling, the sampler is inserted into the sediment.

For groundwater sampling, the sampler is lowered into the well using a cable and positioned within the screened interval, the cable is then fixed to the outside of the well for the time of deployment.

Sample Processing and Analysis:

After retrieval, passive samplers are gently shaken to remove excess water, then packed in Ziploc bags and on ice and sent to the laboratory where they are disassembled to recover the sorbent. The sorbent is then extracted which results in the formation of a solution with significantly higher analyte concentrations compared to the sampled medium, allowing for much lower detection limits compared to standard water analyses (standard analysis methods are USEPA Method 537 and ASTM D7979-16), and analyzed in a laboratory. The concentration of PFAS in the sorbent can then be converted to the concentration of PFAS in the sampled water by using laboratory derived polymer-water partition coefficients.

Examples

The experimental data described below provides sorption characterization data of the used polyurethane foams. The data include: comparison of the initial uptake kinetics in static vs. vibrated system (two analytes); adsorption kinetics in 22-day exposures (15 analytes); adsorption isotherms (15 analytes), the effect of the water parameters on PFAS partitioning investigation, extraction efficiency determination, and field demonstration study results. The analytes targeted in the experiments are listed in Table 1.

TABLE 1

List of PFAS analytes tested for in examples.

| Analytes Abbreviation | Analyte Full Name | CAS No. |
|---|---|---|
| PFBA | Perfluoro-n-butanoic acid | 375-22-4 |
| PFHxA | Perfluororhexanoic acid | 307-24-4 |
| PFHpA | Perfluoroheptanoic acid | 374-85-9 |
| PFOA | Perfluorooctanoic acid | 335-67-1 |
| PFNA | Perfluorononanoic acid | 375-95-1 |
| PFDA | Perfluorodecanoic acid | 335-76-2 |
| PFUnA | Perfluoroundecanoic acid | 2058-94-8 |
| PFDoA | Perfluorododecanoic acid | 307-55-1 |
| PFBS | Perflurorbutanesulfonic acid | 375-73-5 |
| PFHxS | perfluoro-1-hexanesulfonate | 3781-99-6 |
| PFOS | Perfluorooctanesulfonic acid | 1763-23-1 |
| PFDS | Perfluoro-1-decanesulfonate | 2806-15-7 |
| 6:2 FTS | 1H,1H,2H,2H-Perfluorooctane sulfonate | 27619-97-2 |
| 8:2 FTS | 1H,1H,2H,2H-Perfluorodecane sulfonate | 39108-34-4 |
| N-MeFOSAA | N-methylperfluoro-1-octanesulfonamido-acetic acid | 2355-31-9 |
| N-EtFOSAA | N-ethylperfluoro-1-octanesulfonamido-acetic acid | 2991-50-6 |

Materials:

All experiments were conducted in high-density polyethylene (HDPE) bottles or polypropylene (PP) tubes. All solvents were HPLC grade. The PFAS analytes were purchased as a neat material or in methanolic solutions from Sigma Aldrich or Wellington Laboratories. All stock solutions were prepared in methanol.

Sorbent Preparation:

The experiments were conducted using the same two types of reticulated PUF as described above. One PUF was ester-based and the other one was ether-based. The PUF was cut to 5 cm×5 cm size for the vibration experiments and to ~1 cm×1 cm size for all other experiments, then cleaned by three consecutive soaks in HPLC grade methanol with orbital shaker agitation. The first soak was overnight, followed by solvent replacement, 2-hour soak, another solvent replacement and finally 1-hour soak. After that, the solvent was drained and the PUF was dried in the fume hood, then packed in clean HDPE bottle until needed.

Analytical Methods:

All samples were analyzed following serial dilution as per the DoD Quality Systems Manual 5.1 Table B-15 criteria for samples of known high PFAS concentrations using liquid chromatography tandem mass spectrometry (LC-MS/MS) using negative electrospray mode and the analytes quantified using the isotope dilution method.

Effect of Vibration on Uptake Kinetics

To evaluate the effect of vibration on the uptake of PFAS from water, adsorption kinetics of perfluorooctanoic acid (PFOA) and perfluoroactanesulfonic acid (PFOS) were determined in duplicates in vibrated and non-vibrated exposures for both foams. The static experiments were conducted by immersing 5×5 cm pieces of precleaned ester- or ether-based PUF in 500 mL of either PFOS (concentration ~10 ug/L) or PFOA (concentration ~5 ug/L) with 0.01 M NaCl as a background electrolyte. For the vibrated experiments the setup was the same except that the foam was attached to a vibrational device consisting of a sonic toothbrush which provided side to side vibration. The solutions in both static and vibrated modes were sampled at 0, 4, 8, 16, 32, and 64 minutes.

Figure 13:
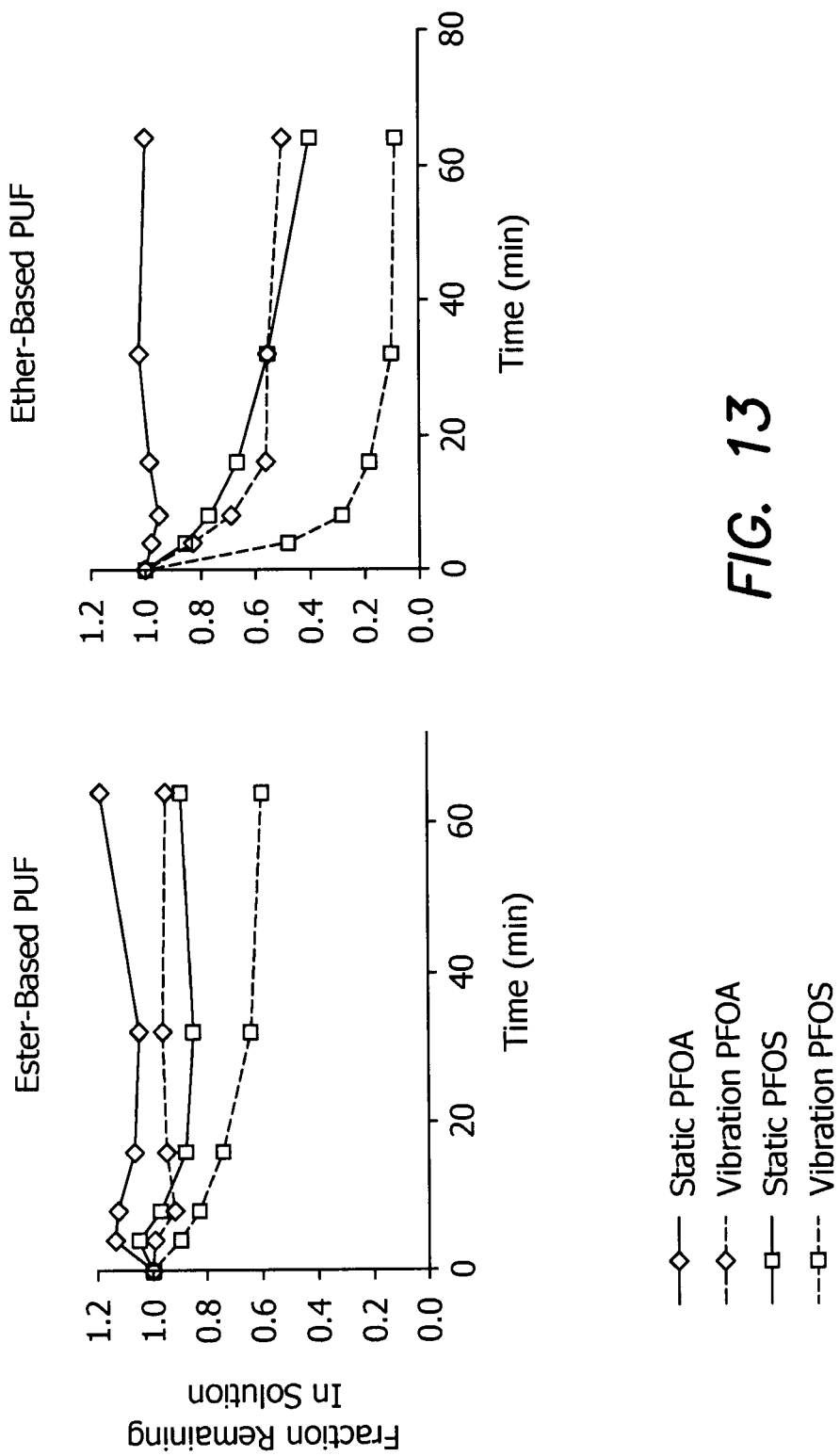
FIG. 13 shows data comparing adsorption results with and without a vibratory motor.

The results of the experiment are presented in FIG. 13 showing that the uptake of PFOA is slower than uptake of PFOS for both ester- and ether-based PUF, and that the ether-PUF adsorbs both the analytes faster than the ester PUF. The use of vibration significantly enhances the mass transfer and allows to adsorb about twice as much of the analytes than would be adsorbed in the static experiments for both PUFs, however, the data for ester-PUF carries more uncertainty because little adsorption was achieved within the experiment duration, so longer experiment would be needed to collect better data.

Adsorption Kinetics Experiments

Adsorption kinetics experiments were conducted in water solutions of PFAS at concentrations of ~100 µg/L of each analyte, except for PFDS, N-MeFOSAA and N-EtFOSAA, which were present at concentrations of ~10 µg/L due to limited amount of the reagents available. The experiments were conducted in triplicates of 125 mL HDPE bottles, with duplicate controls alongside. First, 125 mL of 0.01M NaCl (background electrolyte) in Milli-Q water was added to each bottle. Eight bottles were then spiked with concentrated methanolic stock solutions of the analytes (three bottles for ester-PUF uptake, three bottles for ether-PUF uptake, and two bottles as positive controls (PFAS but no PUF)). With the total spike volume equal of less than 188 µL per bottle, the effect of methanol on the partitioning behavior of PFAS is assumed to be negligible. Negative controls contained 125 mL of 0.01M NaCl and 188 µL of pure methanol; two negative controls contained no PFAS and no PUF, two contained no PFAS but did contain ester-PUF, and two controls contained no PFAS but did contain ether-PUF. The solutions were prepared 1 day before adding PUF and were places on a shaker table to allow for thorough mixing before PUFs were added.

On the first day of the experiment, all solutions were sampled by collecting 500-uL sample (t=0). The experiment time count started when PUF was added. After adding PUF the bottles were placed on the orbital shaker at 130 rpm. The samples (bottles with PFAS and PUF) were sampled after 8 hours, 1 day, 2 days, 6 days, 13 days, and 22 days. The controls were sampled at time 0, 13 days, and 22 days. After experiment termination, the pieces of PUF were air dried and weighed.

Figure 14:
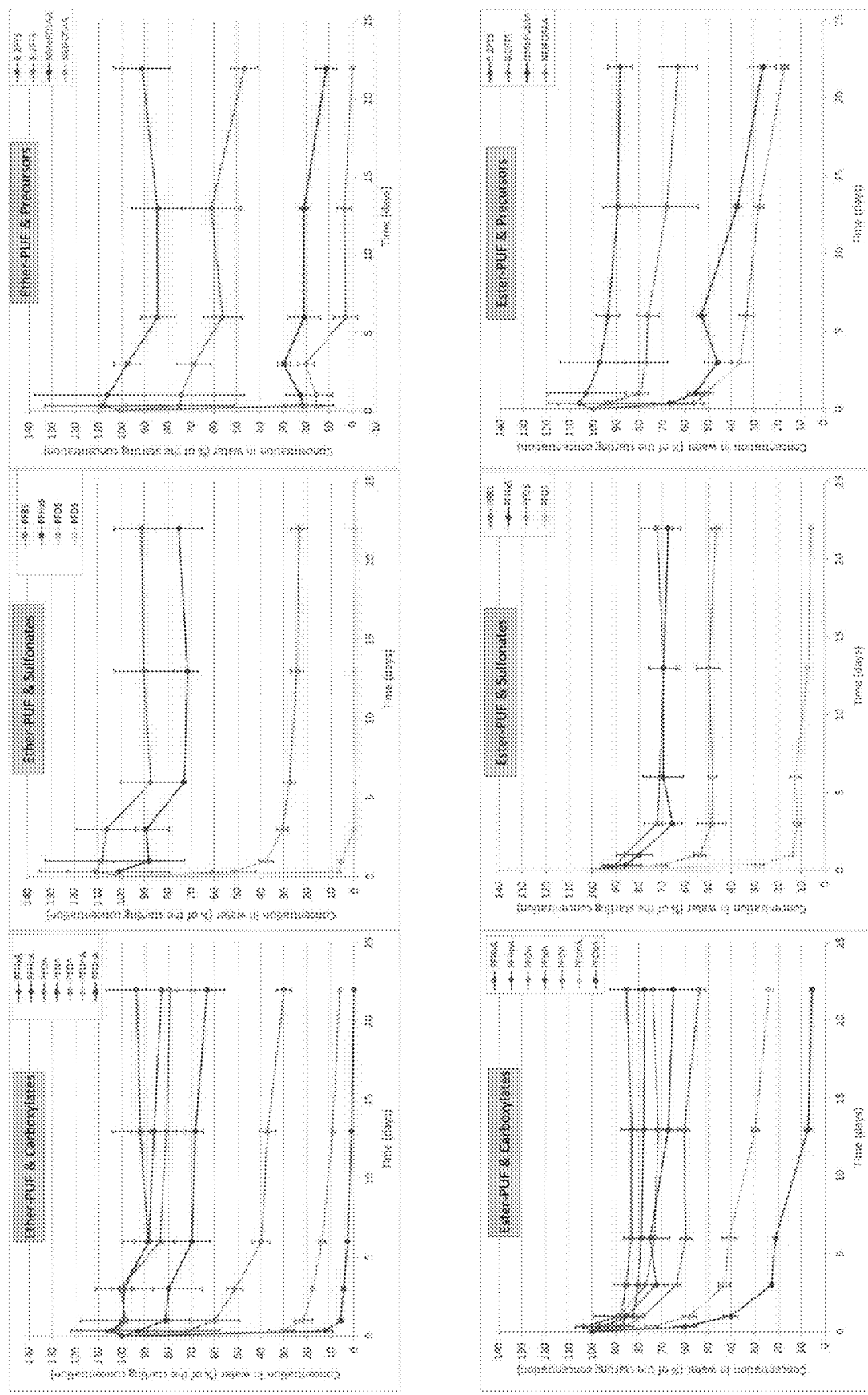
FIG. 14 shows kinetics of PFAS transfer from the water phase to ether-PUF (top row) and ester-PUF (bottom row). All data presented as % of the starting concentration. The error bars are ±1 standard deviation from triplicates. Within each figure, analytes are sorted from the shorter chain lengths on top of the legend to longer chains at the bottom.

Adsorption kinetics varied significantly between analytes and PUF types (FIG. 14). Most of the analytes displayed a rapid uptake by both PUFs and achieved equilibrium in less than a week. Sulfonates were generally adsorbed more efficiently than carboxylates, for example PFOS (sulfonate; carbon chain length equals 8; C8) showed much faster and stronger adsorption than C8 carboxylate, PFOA. The most significant factor determining the adsorption seemed to be the length of the carbon chain, with long chain compounds from carboxylate, sulfonate, and precursor groups showing the strongest and most rapid adsorption (note that the compounds within each graph of FIG. 14 are sorted from the shortest carbon chain length on top of the legend to the longest chain on the bottom). Note that no significant change in PFAS concentration was observed in the positive controls meaning that the loss of PFAS from the water phase during the experiments was due to adsorption not the PUF, and not due to degradation of the analytes or sorption to the bottle. Additionally, no leaching of any of the analytes was observed in the negative controls.

The uptake kinetics were modeled using pseudo-second order kinetic model following the linearization procedures described in Rout et al. (2015):

$$\frac{t}{C_s} = \frac{1}{kC_e^2} + \frac{t}{C_e} = \frac{1}{v_0} + \frac{t}{C_e}$$

where t is the time (d), $C_s$ is the concentration of the analyte in the solid phase (µg/g), k is the kinetic rate constant (g/µg/d), $C_e$ is the concentration of the analyte at equilibrium (µg/g) and $v_0$ is the initial sorption rate (µg/g/d).

In addition to, or as an alternative to, any of the descriptions, the sorbents and/or inventive method can be characterized by the kinetic data presented here. For example, the invention can be described as a method (or sorbent) characterizable by one, or any combination, of the values in Tables 2, 4, or 5. This description can be based on ±50%, or ±30%, or ±20% of any of these values. For example, the sorbent, or the sorbent in a method, can be described as characterizable as having a $C_e$ for PFHxA of 59.3±50% (89.0 to 29.6). $C_e$ is measurable by the techniques described herein and in the equation above. This characterization can be in place of, or in addition to, describing a composition of the sorbent. Or a $C_e$ for PFHxA of 59.3±50%, and a $C_e$ for PFOA of 146.7±50%. Or a $C_e$ for PFHxA of 59.3±50%, and a $C_e$ for PFOA of 146.7±50%, and a $C_e$ for PFOS of 411.2±50%. These are merely examples, the invention can be described as characterizable by one, or any combination of the $C_e$ values in Table 2. The above-described characterizations used $C_e$; however, it should be understood that the method could alternatively be characterized as utilizing a sorbent characterizable by k or $v_o$ in the equation above.

The ±50% range is selected as reasonably supported by the data in view of the experimental error of the described measurement techniques as well as the ability of workers in this area to modify the sorbent through routine experimentation using the descriptions provided here. The Langmuir-related values for 6:2 FTS, NMeFOSAA, NEtFOSAA, PFDS, PFUnA, and PFDoA are excluded from the characterization of the invention because the uncertainty in these values is too great.

Figure 15:
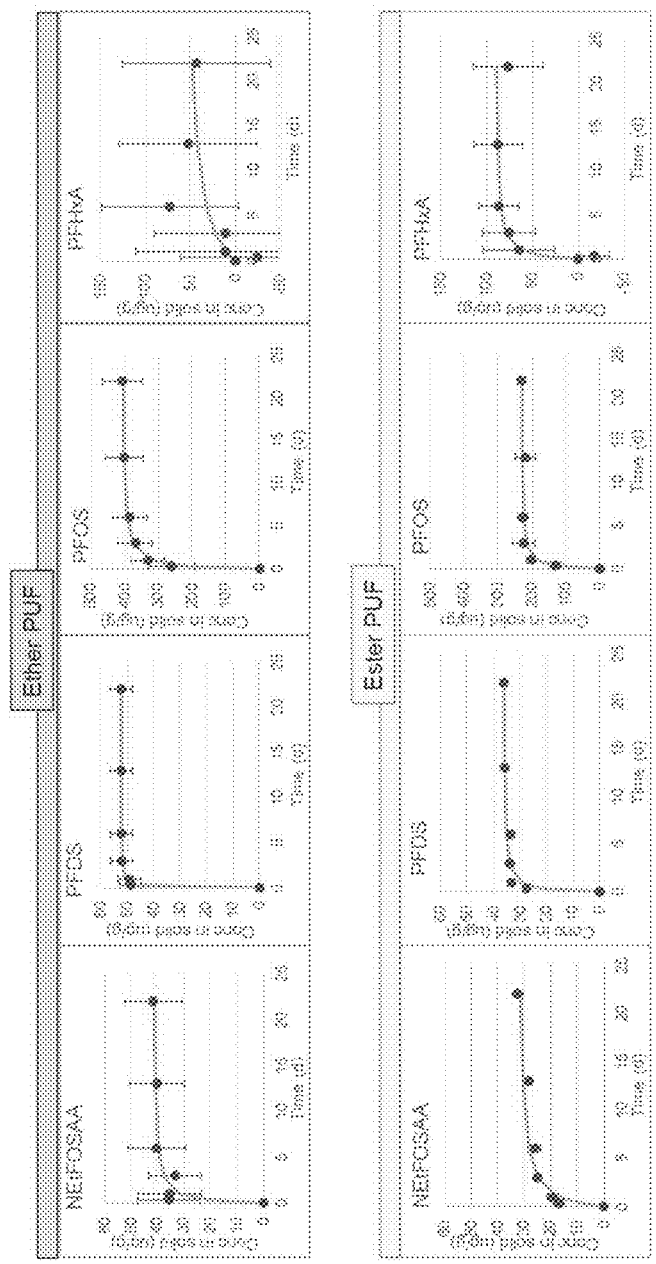
FIG. 15 shows pseudo second order kinetics modeling results for selected PFAS analytes.

Sorption of all analytes to both types of PUF was well modeled by the pseudo-second order kinetic model except the sorption of 6:2 FTS and PFHxS onto ester PUF, which showed significant scatter of the collected data and therefore increased uncertainty of the obtained results. Modeling results for select analytes are shown in FIG. 15. Sorption parameters for all analytes to both PUFs are presented in Table 2, where analytes in each group are sorted from the shorter chains on top to the longer chains at the bottom. Comparison of the kinetic model parameters ($C_e$ and k, and $v_o$) between the two sorbents show that while the two sorbents display similar behavior, ether PUF shows slightly stronger sorption of longer chain analytes, whereas ester PUF performs slightly better for some of the shorter chain analytes (e.g. PFHxA or PFBS).

TABLE 2

Parameters of the sorption kinetics of PFAS to ether and ester PUFs.

| | Ether PUF | | | Ester PUF | | |
|---|---|---|---|---|---|---|
| Analytes | $C_e$ (µg/g) | k (g/µg/d) | $v_0$ (µg/g/d) | $C_e$ (µg/g) | k (g/µg/d) | $v_0$ (µg/g/d) |
| Carboxylates | | | | | | |
| PFHxA | 59.3 | 0.0033 | 11.7 | 90.3 | 0.0249 | 203.1 |
| PFHpA | 120.7 | 0.0011 | 16.7 | 105.2 | 0.0096 | 106.0 |
| PFOA | 146.7 | 0.0013 | 27.2 | 132.5 | 0.0127 | 223.5 |
| PFNA | 228.0 | 0.0025 | 132.4 | 183.0 | 0.0039 | 129.6 |
| PFDA | 366.3 | 0.0027 | 368.9 | 210.6 | 0.0043 | 189.0 |
| PFUnA | 432.7 | 0.0068 | 1270.3 | 301.7 | 0.0029 | 260.8 |
| PFDoA | 352.3 | 0.0260 | 3230.3 | 278.9 | 0.0047 | 362.7 |
| Sulfonates | | | | | | |
| PFBS | 41.0 | −0.0104 | −17.5 | 123.0 | 0.0200 | 333.6 |
| PFHxS | 173.9 | 0.0012 | 36.7 | 150.2 | 0.0168 | 378.5 |
| PFOS | 411.2 | 0.0082 | 1380.1 | 231.3 | 0.0192 | 1025.0 |
| PFDS | 52.4 | 0.7250 | 1987.5 | 36.5 | 0.1274 | 169.5 |
| Precursors | | | | | | |
| 6:2 FTS | 45.7 | 0.0039 | 8.1 | 40.1 | 0.0022 | 3.6 |
| 8:2 FTS | 275.9 | 0.0028 | 214.5 | 147.4 | 0.0032 | 70.2 |
| NEtFOSAA | 41.9 | 0.0730 | 128.1 | 32.7 | 0.0320 | 34.7 |
| NMeFOSAA | 48.5 | 0.0423 | 99.4 | 42.0 | 0.0170 | 29.5 |

Extraction Efficiency Determination (PUF Extractions)

Two sets of extraction efficiency experiments were conducted. In the first set (experiment No. 1), extraction of all 15 analytes listed in Table 1 from both types of PUF (ether and ester based) was investigated. First, the two types of PUF were contaminated (loaded) with the analytes of interest. The loading step was conducted by immersing of ester-PUF or ether-PUF in aqueous PFAS solution with analytes concentrations of ~1000 µL/L (each analyte except PFDS, N-MeFOSAA and N-EtFOSAA which were present at concentrations of ~50 µg/L each). The solutions were sampled before adding PUF and then again after 8 days of PUF loading on the orbital shaker to determine the initial starting concentration of PFAS on PUF based on the total weight of PUF in each bottle. When loading was completed the PUFs were quickly rinse, dried with paper towels to remove excess water and then placed in the extraction vessels.

Triplicated extractions were conducted for each PUF using five solvents: 0.4% (v/v) ammonia in methanol, 0.4% (v/v) in ethanol, 200 mM NaOH in methanol, 200 mM NaOH in ethanol, and 0.1% (v/v) monoethylamine (MEA) in methanol. Extraction of each sample consisted of three consecutive extraction steps with 4-5 mL of solvent and each extraction step was conducted using 30 minutes of sonication followed by 30-120 minutes of agitation on an orbital shaker. At the end, all three extracts from the same piece of PUF were combined together and analyzed for PFAS concentration and the PUF itself was air dried and weighed to determine the sorbent weight.

The extraction efficiency for each analyte was calculated as the ration between the amount of analyte in the solvent post extraction to the amount of analyte adsorbed to PUF during the initial loading step (i.e., the initial amount of PFAS on PUF before extraction). For some analytes (particularly the shorter chains) very little adsorption was observed during the loading process. If the difference between the final and initial concentration of an analyte in the loading solution was less than 10%, that analyte was excluded from the extraction efficiency cautions to avoid overinterpretation of marginally significant results. The extraction efficiency experiments for these analytes were determine for ether-PUF only in a separate experiment (experiment No. 2) where only the analytes with weaker adsorption were used. This experiment is described below, and the combined extraction efficiency results from the two sets of experiments are presented in Table 3 and discussed in the following paragraph. One important observation from the first extraction experiment was that the ester PUF was broken down by ammonia in methanol and by NaOH in both methanol and ethanol, disabling accurate PUF weight determination post-extraction, so these solvents are not compatible with ester PUF. Ester PUF is therefore preferably extracted with MEA in methanol or ammonia in ethanol. For ether PUF, ammonia in methanol is a preferred solvent because both ammonia and methanol are used in the standard soil extraction methods and therefore are guaranteed not to interfere with the analytical method.

The second extraction efficiency experiment (experiment No. 2) focused on investigation the extraction of the shorter chain (weaker adsorption) analytes only. The goal of this experiment was also to optimize the extraction procedures by determining if certain steps (e.g., sonication) are useful or not. First, a batch of the ether-PUF was contaminated with PFHxA, PFHpA, PFOA, PFNA, PFBS, PFHxS, PFOS, 6:2FTS and 8:2FTS. Spiking solution samples were taken at the beginning and end of spiking to allow calculation of the loading or initial concentration of PFAS in PUF (ng of PFAS per gram of PUF). Unless otherwise noted, the PUF was then retrieved and quickly rinsed with Milli-Q water to remove any unbound analytes and dried off with paper towels. The PUF was then subjected to the following extractions:

0.4% ammonia in methanol with sonication (sonication treatment defined as three consecutive extractions with 5 mL of solvent and 30-45 minutes of sonication followed by 30-120 minutes of agitation on an orbital shaker)

0.4% ammonia in methanol with shaking only (shaking treatment defined as three consecutive extractions with 5 mL of solvent; no sonication, one overnight extraction with agitation on an orbital shaker followed by two shorter extractions [180 and 30 minutes] on an orbital shaker)

0.4% ammonia in ethanol with sonication (as defined above)

0.4% ammonia in ethanol with shaking only (as defined above) Unrinsed PUF (just dried with paper towels) extracted with 0.4% ammonia in methanol with shaking only treatment (as defined above)

After analyzing the extraction solvents, the amount of PFAS desorbed from PUF was compared to the initial loading of PFAS in PUF to calculate the extraction efficiency (expressed in percent). All treatments yielded statistically similar results, and that the extraction efficiencies for most analytes were in the desired range of 100+/−20%. Sonicated ethanol treatment yielded results above 120% for some analytes indicating potential influence of the solvent on the analytical run, so ethanol should be avoided. Rinsing has no significant effect on the results meaning that simply removing majority of the water attached to PUF with a clean paper towel removed most of the unadsorbed PFAS and the rinsing step is not necessary. Both sonicated and shaken only treatments in methanol achieved similar results; for simplicity, shaking only is recommended because it avoid multiple transfers of the sample between sonicator and orbital shaker.

The results are presented in the table below.

TABLE 3

Extraction efficiencies for all analytes, combined from two sets of experiment described in text.

| Experiment | Analyte | Average extraction efficiency (%) | Standard deviation |
|---|---|---|---|
| No. 2 | PFHxA | 98 | 8 |
| No. 2 | PFHpA | 105 | 4 |
| No. 2 | PFOA | 110 | 6 |
| No. 2 | PFNA | 95 | 24 |
| No. 2 | PFBS | 78 | 15 |
| No. 2 | PFHxS | 105 | 22 |
| No. 2 | PFOS | 86 | 21 |
| No. 2 | 6:2FTS | 130 | 8 |
| No. 2 | 8:2FTS | 83 | 12 |
| No. 1 | PFDA | 80 | 6 |
| No. 1 | PFUnA | 76 | 6 |
| No. 1 | PFDoA | 90 | 9 |
| No. 1 | NMeFOSAA | 103 | 10 |
| No. 1 | NEtFOSAA | 96 | 3 |
| No. 1 | PFDS | 78 | 3 |

Adsorption Isotherm Experiments

Adsorption isotherm experiments were conducted to provide sorption characteristics of the chosen polyurethane foams. The experiments were conducted in 125 mL HDPE bottles, which were filled with 125 mL of PFAS solution in 0.01M NaCl (background electrolyte) with varying PFAS concentrations, sampled to determine the starting PFAS concentration, and then a 1 cm×1 cm piece of ester- or -ether PUF was placed in each bottle. The bottles were then closed and placed on an orbital shaker for 21 days.

The starting concentrations of PFAS in the adsorption experiment were 0.05; 0.1; 0.5; 2; 10; 50; and 500 µg/L of each analyte except PFDS, N-MeFOSAA and N-EtFOSAA which were added at approximately 1/10th of these concentrations due to analyte stock amount limitation. Alongside samples, positive controls (2 of 50 µg/L of PFAS but no PUF) and negative controls (no PUF and no PFAS; only ester-PUF; only ether PUF) were prepared. The low concentration bottles (negative controls and concentrations 0.05-2 µg/L) were sampled in through solid phase extraction (SPE) which consumes the sample, so duplicated bottles were prepared for the initial and final concentration measurements. The higher concentration samples were sampled by removing small volume (0.5 mL) of the sample at the experiment initiation and then again at termination; these samples were analyzed using direct injection method. Direct injection samples were preserved with 0.5 mL of methanol and then diluted as needed to fit the range of the method calibrations. All SPE samples were analyzed in duplicates and the direct injection samples were analyzed in triplicates except the two positive controls which were analyzed through direct injection in duplicates. The difference in the initial and final concentrations of PFAS in the tested solutions was used to estimate the amount of the analytes adsorbed to the PUF, which was then converted to ng/g by dividing by the PUF weight determined post-experiment after air-drying. The results were modeled using two adsorption models: Langmuir and Freundlich. Langmuir model following the equation:

$$q = q_{max} \frac{K_L C}{1 + K_L C}$$

where:

q is the equilibrium amount of analyte on the sorbent (µg/g)

$q_{max}$ is the sorption capacity of PUF (µg/g)

$K_L$ is the Langmuir adsorption equilibrium constant (L/g)

C is the equilibrium aqueous concentration of analyte (µg/L)

Freundlich model followed the equation:

$$q = K_F C^n$$

where:

$K_F$ and n are the Freundlich adsorption constants.

Figure 16:
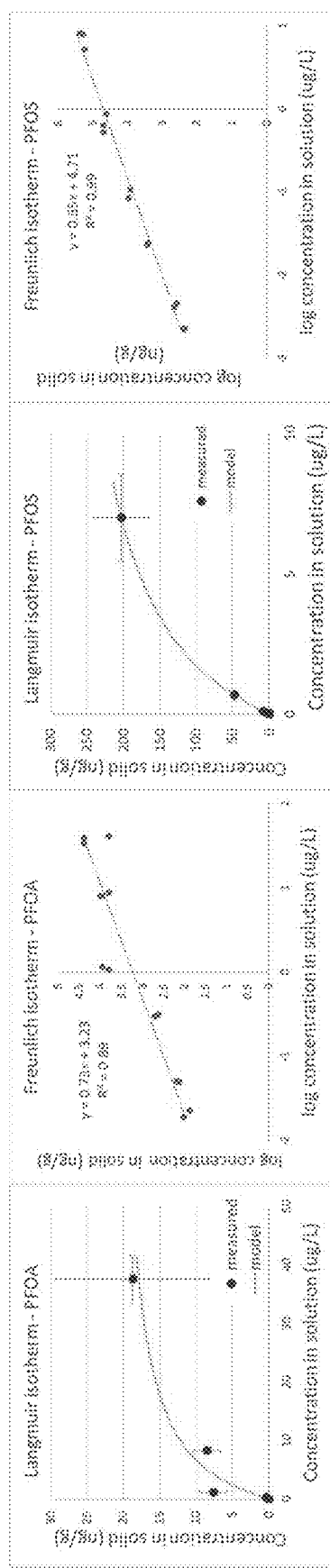
FIG. 16 shows Langmuir and Freundlich adsorption isotherms for select analytes onto ether polyurethane foam.
Figure 17:
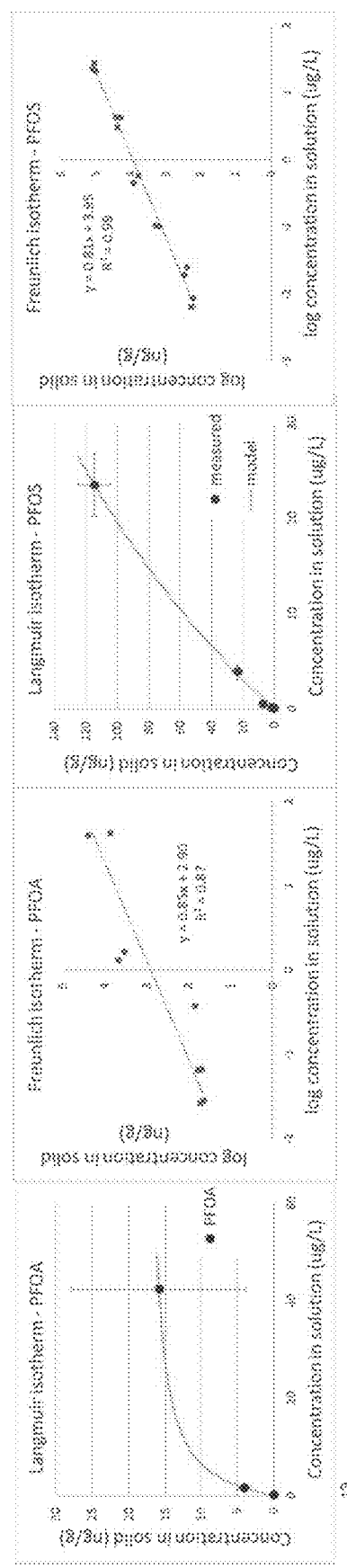
FIG. 17 shows Langmuir and Freundlich adsorption isotherms for select analytes onto ester polyurethane foam.

The data were modeled successfully using the abovementioned models for starting water concentrations up to 50 µg/L. The highest starting concentration (500 µg/L) plotted above the isotherms fitted through the remaining data. Such an increase in adsorption at higher concentrations is indicative of a second layer formation (adsorption of the analyte from solution to the analyte already adsorbed to the sorbent), which cannot be described properly with Langmuir or Freundlich isotherms, so this concentration was excluded from the modeling presented below. The example of Langmuir and Freundlich fit to the data for ether and ester PUFs are shown in FIGS. 16 and 17, respectively, and the adsorption isotherm parameters for Langmuir and Freundlich models for ether- and ester-based PUFs and all analytes are summarized in Table 4.

TABLE 4

Adsorption isotherm coefficients for ether- and ether-PUF.

| | | Langmuir | | Freundlich | | | Langmuir | | Freundlich | | |
|---|---|---|---|---|---|---|---|---|---|---|---|
| | Carbon | $K_L$ | $q_{max}$ | $K_F$ (ng/g)/ | | | $K_L$ | $q_{max}$ | $K_F$ (ng/g)/ | | |
| Analyte | chain length | L/kg | µg/g | (µg/L)$^n$ | n | $R^2$ | L/kg | µg/g | (µg/L)$^n$ | n | $R^2$ |
| | | | | Ether PUF | | | | | Ester PUF | | |
| Precursors | | | | | | | | | | | |
| 6:2 FTS | 6 | 0.0014 | 965,991 | 930 | 0.95 | 0.9531 | 0.0011 | 331,927 | 350 | 0.89 | 0.8407 |
| 8:2 FTS | 8 | 168 | 61 | 5,618 | 0.80 | 0.9689 | 0.0027 | 557,068 | 1,299 | 0.86 | 0.8303 |
| NMeFOSAA | 8 | 1,506 | 29 | 19,684 | 0.88 | 0.8848 | 0.0336 | 83,303 | 1,458 | 0.87 | 0.8545 |
| NEtFOSAA | 8 | 2,011 | 36 | 33,051 | 0.85 | 0.8726 | 0.0067 | 511,434 | 2,395 | 0.92 | 0.9202 |
| Sulfonates | | | | | | | | | | | |
| PFBS | 4 | 146 | 7 | 525 | 1.08 | 0.9421 | 68 | 28 | 626 | 0.94 | 0.9390 |
| PFHxS | 6 | 20 | 135 | 3,331 | 0.80 | 0.9785 | 194 | 19 | 1,139 | 0.74 | 0.8299 |
| PFOS | 8 | 271 | 310 | 51,852 | 0.85 | 0.9865 | 16 | 421 | 8,963 | 0.81 | 0.9856 |
| PFDS | 10 | NA | NA | 36,937 | 0.58 | 0.7638 | 78 | 618 | 29,933 | 0.84 | 0.9727 |
| Carboxylates | | | | | | | | | | | |
| PFHxA | 6 | 230 | 15 | 638 | 0.88 | 0.8385 | 333 | 12 | 538 | 0.99 | 0.8708 |
| PFHpA | 7 | NA | NA | 837 | 0.84 | 0.8257 | 139 | 24 | 683 | 0.91 | 0.8993 |
| PFOA | 8 | 128 | 22 | 1,696 | 0.73 | 0.8918 | 200 | 18 | 803 | 0.85 | 0.8658 |
| PFNA | 9 | 52 | 110 | 5,724 | 0.79 | 0.9937 | 163 | 17 | 1,159 | 0.71 | 0.9443 |
| PFDA | 10 | 134 | 225 | 23,026 | 0.81 | 0.9948 | 65 | 74 | 2,765 | 0.70 | 0.8914 |
| PFUnA | 11 | 141 | 708 | 78,352 | 0.85 | 0.9877 | 0.00009 | 91,529,204 | 9,189 | 0.84 | 0.9831 |
| PFDoA | 12 | 25 | 14,944 | 243,232 | 0.95 | 0.8883 | 0.00034 | 77,371,833 | 20,368 | 0.95 | 0.9767 |

Distribution (also known as partition) coefficients ($K_d$s) were also determined for the linear part of the data (lower concentrations). The distribution coefficients provide a scaling factor that allows passive sampler results ($C_s$, in mass of analyte per gram of passive sampler) to be converted to water concentrations in the sampled water ($C_w$, in mass of analyte per volume of water), as shown below:

$$C_w = \frac{C_s}{K_d}$$

Figure 18:
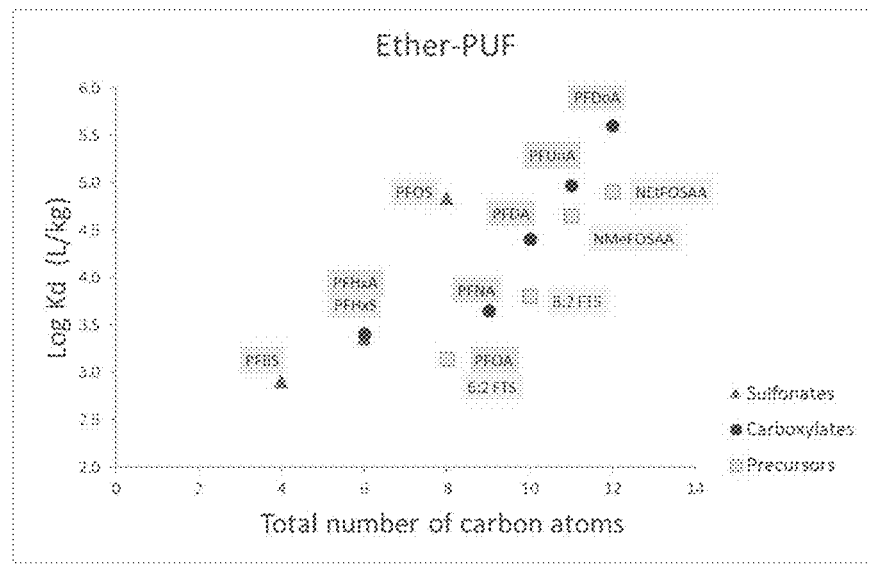
FIG. 18 shows Langmuir and Freundlich adsorption isotherms for select analytes onto ether polyurethane foam.
Figure 19:
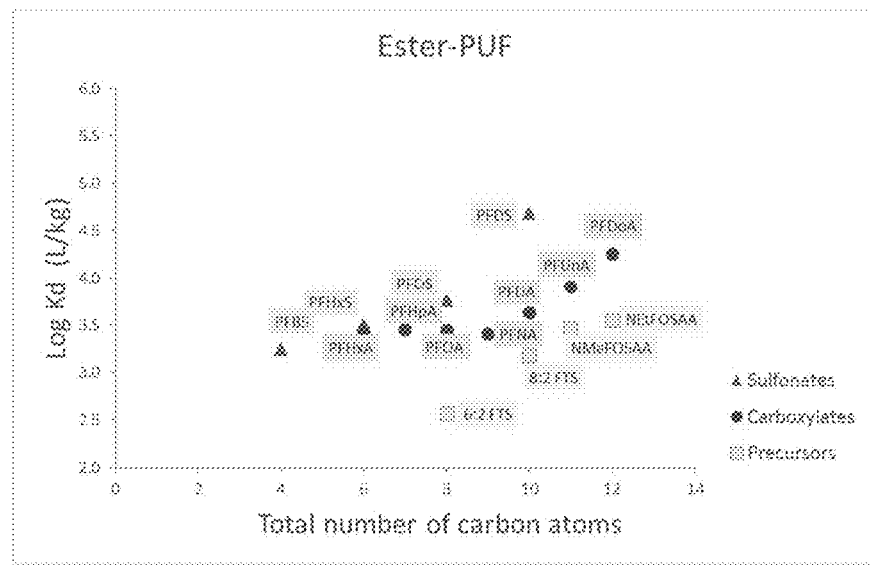
FIG. 19 shows Langmuir and Freundlich adsorption isotherms for select analytes onto ester polyurethane foam.

The distribution coefficient is defined as the ratio of the amount or concentration analyte in/on solid to the amount or concentration of the analyte in liquid, and as such the concept of distribution coefficient only applied to the range of concentrations in which the concentration of the analyte in the sorbent is linearly proportional to the concentration of the analyte in water (the uptake is not concentration depended). For data that follow a non-linear adsorption isotherm (such as Langmuir and Freundlich), the distribution coefficients can be determined from the lower range of concentrations in which the linearity exists. In our data, the linear range was observed for up to 2-10 µg/L of the initial PFAS concentration. The obtained distribution coefficients are summarized in Table 5. It can be seen that the $K_d$ generally increases with the length of the carbon chain. Also, for the same carbon chain length, sulfonate species have higher $K_d$ than carboxylate species. Log $K_d$ values for each of the analyte groups investigated in this study (precursors, sulfonates, and carboxylates) correlate almost linearly with the total number of carbon atoms in the analyte (which for the sulfonates and carboxylates is the same as the length of the main carbon chain) (FIGS. 18 and 19). The exception are the shorter chain carboxylates: PFHxA (C6) for ether-PUF and PFHxS, PFHpS, and PFOS (C6, C7, and C8, respectively) for ester-PUF. From the comparison of $K_d$ values for ether- and ester-PUF it is also apparent that the ether-PUF shows stronger adsorption than ester-PUF.

TABLE 5

Distribution coefficients ($K_d$s) for ether- and ester-based polyurethane foams.

| Analyte | Main carbon chain length | Total number of carbon atoms | $K_d$ for Ether-PUF | $K_d$ for Ester-PUF | Log $K_d$ for Ester-PUF | Log $K_d$ for Ether-PUF |
|---|---|---|---|---|---|---|
| Precursors | | | | | | |
| 6:2 FTS | 6 | 8 | 1,380 | 371 | 3.14 | 2.57 |
| 8:2 FTS | 8 | 10 | 6,415 | 1,531 | 3.81 | 3.18 |
| NMeFOSAA | 8 | 11 | 44,716 | 2,895 | 4.65 | 3.46 |
| NEtFOSAA | 8 | 12 | 80,145 | 3,531 | 4.90 | 3.55 |
| Sulfonates | | | | | | |
| PFBS | 4 | 4 | 813 | 1,769 | 2.91 | 3.25 |
| PFHxS | 6 | 6 | 2,277 | 3,218 | 3.36 | 3.51 |
| PFOS | 8 | 8 | 69,709 | 5,881 | 4.84 | 3.77 |
| PFDS | 10 | 10 | NA | 48,940 | NA | 4.69 |
| Carboxylates | | | | | | |
| PFHxA | 6 | 6 | 2,529 | 2,750 | 3.40 | 3.44 |
| PFHpA | 7 | 7 | NA | 2,868 | NA | 3.46 |
| PFOA | 8 | 8 | 1,355 | 2,805 | 3.13 | 3.45 |
| PFNA | 9 | 9 | 4,501 | 2,544 | 3.65 | 3.41 |
| PFDA | 10 | 10 | 25,253 | 4,340 | 4.40 | 3.64 |
| PFUnA | 11 | 11 | 93,725 | 8,070 | 4.97 | 3.91 |
| PFDoA | 12 | 12 | 400,567 | 18,061 | 5.60 | 4.26 |

Effect of Geochemical Factors on $K_d$

Partitioning between natural waters and various solids for most environmental contaminants is affected by certain geochemical characteristics of the water, which can include pH, ionic strength, total and dissolved organic carbon, temperature, and others. The effect of geochemical factors, including ionic strength and dissolved organic carbon (DOC) concentration was investigated. The experiments were analogous to the adsorption isotherm experiments except that variation of the investigated parameters was added. The experiments were conducted with starting PFAS concentration of 2 (low) and 10 (high) μg/L.

Overall, the data presented in more details below shows that the water parameters can affect partioning of PFAS to the passive sampler, so the basic water measurements could be taken to provide the water concentrations using the pH, DOC, and ionic strength adjusted $K_d$ values. To be determine water concentrations ($C_w$) in the sampled water after a passive sampler deployment we use the equation: $C_w=C_s/K_d$; where $C_s$ is the concentration of PFAS in the passive sampler material (PUF).

Ionic Strength

Figure 20:
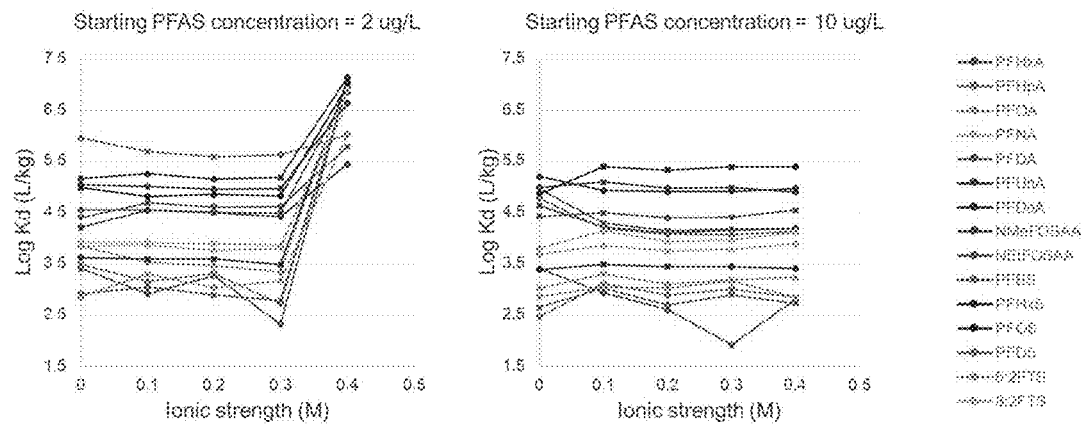
FIG. 20 illustrates the relationship between distribution coefficient ($K_d$) and the total number of carbons in the analyte structure for ether-PUF.
Figure 21:
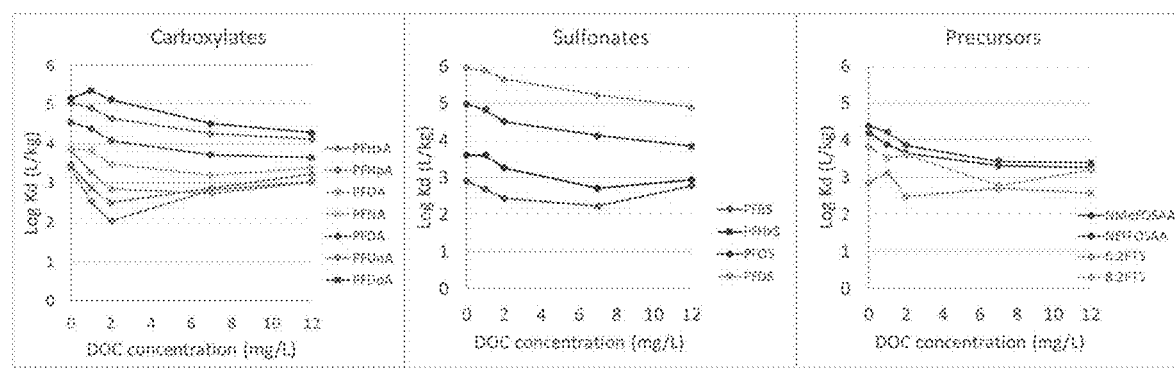
FIG. 21 illustrates the relationship between distribution coefficient ($K_d$) and the total number of carbons in the analyte structure for ester-PUF.

Four ionic strengths were investigated, covering the range of ionic strengths from freshwater to estuarine water. The solutions consisted of 0.1; 0.2, 0.3, and 0.4 M sodium chloride (NaCl). Log $K_d$ values were determined for low and high PFAS treatments for each analyte and ionic strength combination by conducting a one-point regression though the origin on the "amount sorbed vs. amount in solution" (see Langmuir isotherms in FIG. 20). The effect of ionic strength on the log $K_d$ values are presented in the figure below. The plots indicate little impact of the water's ionic strength on $K_d$ except for the highest ionic strength and lower PFAS concentration treatment.

DOC

Four concentrations of DOC were used. The DOC stock solution was prepared from humic acid salt that was mixed with 10 mM monobasic potassium phosphate used as a pH buffer. The mixture was agitated for 24 hours, after which it was centrifuged and then filtered through 0.7 μm glass filter to remove any undissolved particles. So prepared stock solution was used to create working DOC solutions for the experiment. Because the actual humic acid concentration in the humic acid salt neat material may vary, DOC concentration was measured analytically both at the beginning and at the end of the experiment to account for potential DOC loss due to microbial utilization. Starting concentrations of DOC in the four treatments were determined to be 1, 2, 7, and 12 mg/L, which covers a range of typical groundwater and freshwater DOC concentrations, but is lower than typical porewater DOC concentrations. The experiment was prepared both with high (10 μg/L) and low (2 μg/L) starting concentrations of PFAS; however, due to analytical problems only low PFAS concentration data are currently available. The results are shown in the figure below. It can be seen that $K_d$ values vary systematically with DOC concentration, with highest DOC concentration treatments achieving about 0.5-1.0 log unit lower $K_d$ values than in water with no DOC. Further, for carboxylate it is apparent that the relationship between $K_d$ and DOC varies with the PFAS chain length, with the longest chains showing a more even, slight decrease of $K_d$ with increasing DOC, whereas the shortest chain analytes show a more pronounced drop in $K_d$ with low DOC addition but seem to be less affected at high DOC concentrations.

pH

The solutions of varying pH were prepared in MilliQ water with 0.01 M sodium chloride as a background electrolyte. The pH was then adjusted to the desired value by drop by drop additions of 20 mM hydrochloric acid or 20 mM sodium hydroxide while monitoring the pH using a pH meter. Finally, PFAS stock solution was added to the bottles to achieve the starting PFAS concentrations of 2 or 10 ug/L. For each pH and each starting PFAS concentration level, three replicate bottles were prepared (i.e. at pH 4 there were 3 replicates for starting PFAS concentration of 2 ug/L and 3 replicates for starting PFAS concentration of 10 ug/L). Once all the bottles were spiked they were allowed to thoroughly mix on an orbital shaker overnight after which the solutions were sampled (0.5 mL) to determine the time zero concentration of PFAS. A piece of PUF was then added to each bottle and the bottles were placed on the orbital shaker again, where they remained for 23 days to allow equilibration between PUF and the solution. After 23 days, the solutions were sampled again (0.5 mL) and the amount of PFAS on PUF was calculated from the loss of PFAS from solution during the exposure. The PUF was then retrieved and dried to determine its weight so the results can be reported in per gram basis and the solutions were used to determine the final pH through titration. The final pH determination revealed that the pH meter used at experimental setup must have malfunctioned or the solution was not sufficiently mixed before the pH was taken, because the highest pH treatment was about 6 instead of 8. The results cover the range of 4.1 to 6.2. The $K_d$ value was calculated only for analytes that were still detectable in the solution at experiment termination.

The effect of pH on the log $K_d$ values was measured for the starting concentration of PFAS equal to about 2 ug/L ("P=2") and about 10 ug/L ("P=10"). For PFHxA the pH had no impact on $K_d$ whereas for all the other analytes the log $K_d$ decreases with increasing pH. The strength of the effect does not seem to correlate with the PFAS chain length. The average decrease rate of log $K_d$ with pH for all analytes except PFHxA is value decreases on average by 0.52 log units per 1 pH unit. This relationship can be used to select the correct log $K_d$ to match the pH of the sampled environmental water based on the field pH measurement.

Field Demonstration of the PUF-Based Passive Sampler

A field demonstration study was conducted to determine if the developed passive sampler works in more complicated matrices. Presence of fluctuating PFAS concentrations, changing water temperature and ionic strength, a complex aqueous matrix carrying suspended particulates, organic carbon, and dissolved and adsorbed phase co-contaminants can all affect the performance of passive samplers. In surface water, another potential influence is biofouling on the surface of a passive sampler, which can lower the analyte uptake rate.

The field demonstration was conducted at two airport sites, where due to the firefighting training activities elevated levels of PFAS have been identified. Passive samplers were deployed in both surface waters (small creeks and a small river) and in groundwater monitoring wells, using designs of hardware shown above. The surface water sampler holds a piece of PUF 15 cm×15 cm (225 cm$^2$); the groundwater sampler can hold up to three pieces 8×13 cm (104 cm$^2$) each. From laboratory experiments it was determined that about 100 cm$^2$ should collect a comparable amount of PFAS to a standard 250-mL water sample. To evaluate the performance of the passive samplers, grab water samples were collected for PFAS and total organic carbon (TOC) at each sampling station before deploying the passive sampler and again after retrieving it. Additionally, basic geochemical parameters of the water (pH, temperature, conductivity) were measured in situ by the sampling teams. The passive samplers were deployed for four weeks to allow them to equilibrate with the sorbent. Retrieved passive samplers were packed in Ziploc bags and shipped back to the Battelle's Norwell laboratory while still in the hardware so they could be processed in clean conditions at the laboratory. All passive samplers and water samples were packed on ice for transport.

At the laboratory the passive sampler hardware was disassembled to retrieve the PUF. The PUF was inspected and photographed. Paper towels were used to remove excess water and (where present) sediment particles from the PUF. Because the surface water PUF is twice as large as PUF from the surface water was then split in two; one part was submitted for immediate analysis and the other half was archived or submitted for analysis as a replicate sample. From the groundwater samplers, between one and three pieces of PUF were submitted for immediate analysis.

The water samples were extracted and analyzed for following Battelle's standard operating procedure for non-potable waters. For PUF, a modified solids method was used, following a demonstration of capability study on a laboratory spiked PUF. Water results were reported in ng/L whereas the passive sampler results in ng/g. The weight of the passive samplers was determined post-extraction on air-dried samplers. The passive sampler results ($C_s$) were used to calculate the water concentrations (Cw-calc) using the below equation:

$$Cw\text{-}calc\left(\frac{ng}{L}\right) = \frac{C_s\left(\frac{ng}{g}\right) * 1000\left(\frac{g}{kg}\right)}{K_d\left(\frac{L}{kg}\right)}$$

The $K_d$ (often reported in its logarithmic form as log $K_d$) is the solid-water partition coefficient and was determined experimentally for simplified matrix (Milli-Q water and 0.01 M NaCl as a background electrolyte) in batch experiments described in the section called "Adsorption isotherms". The $K_d$ is analyte and water condition specific, for example it can be affected by water temperature, ionic strength, pH, dissolved organic carbon (DOC), etc. The effect of some of these variables was investigated through laboratory experiments in the section "Effect of Geochemical Factors on $K_d$," section, which allows correction of the $K_d$ for the effects of the matrix.

To evaluate the performance of the passive sampler in field deployments, the passive sampler-derived water concentrations (Cw-calc) were compared to the average grab water concentration (Cw-grab) calculated as an average between the concentration of PFAS in the water sample collected before deploying and after retrieving the sampler. This analysis was conducted for the analytes for which the partition coefficients were determined in adsorption isotherm section.

Figure 22:
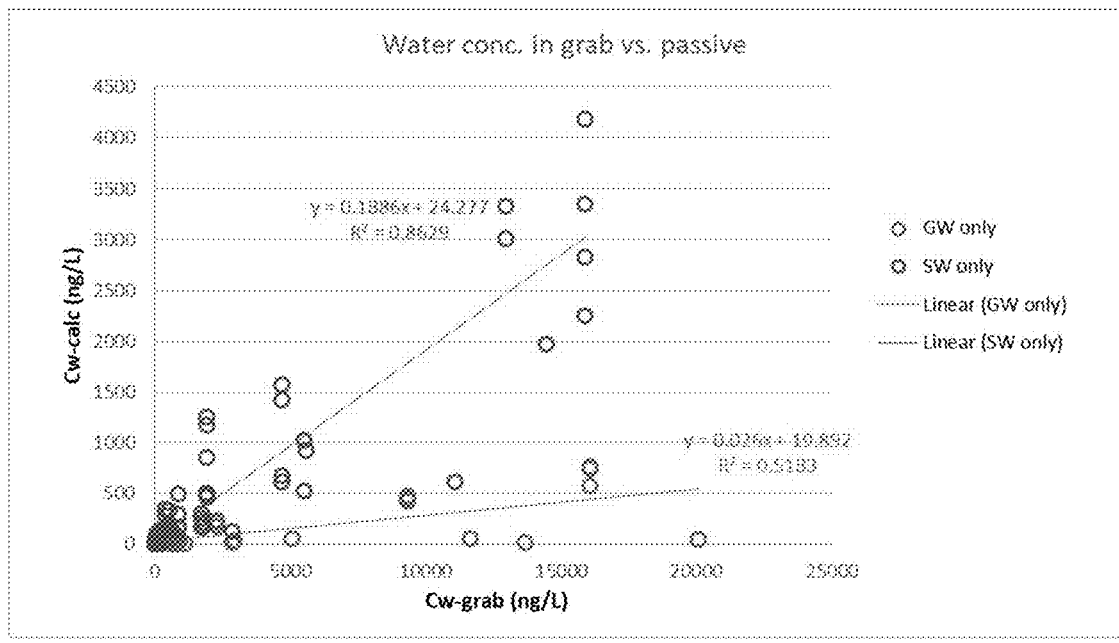
FIG. 22 shows calculated water concentrations (Cw-calc) derived from passive sampler results vs the average deployment and retrieval grab water sample concentrations (Cw-grab). In calculation of the above Cw-calc the $K_d$ in simplified matrix was used. GW—groundwater samples, SW—surface water samples.

When $K_d$ in simplified matrix is used, the Cw-calc account for on average 19% of the Cw-grab in surface water samples (slope of 0.19 and $R^2$ of 0.86) and 3% in groundwater (slope of 0.026 and $R^2$ of 0.52; FIG. 22). Note that each data point in FIG. 1 and all the other figures in this section represent a concentration of one analyte in one sample; for example, the point highest on the Cw-calc axis represents the concentration of PFOS in the bottom half split of the sampler "PF0011". It is also evident that the groundwater samples do not display the same correlation as the surface water samples.

Because Cw-grab and Cw-calc did not agree very well, the effect of the sampled water matrix was investigated. Analysis of the pH, temperature, ionic strength, and TOC showed that all the parameters except for TOC and, in groundwater, the temperature where similar in the simplified matrix from adsorption isotherm experiments and in the waters tested during the field deployments. The TOC in the field waters was about 7 mg/L on average and because DOC was not measured for these field samples it was assumed that the majority of the organic carbon in these samples is dissolved. Based on the laboratory experiment, 7 mg/L of DOC caused an average of 0.8 decrease in the log $K_d$ value compared to the simplified matrix. When that adjusted $K_d$ was used, the Cw-calc and Cw-grab showed a much better agreement, with surface water Cw-calc values averaging 119% of the Cw-grab values, and the groundwater Cw-calc averaging 16% of the Cw-grab values.

Figure 23:
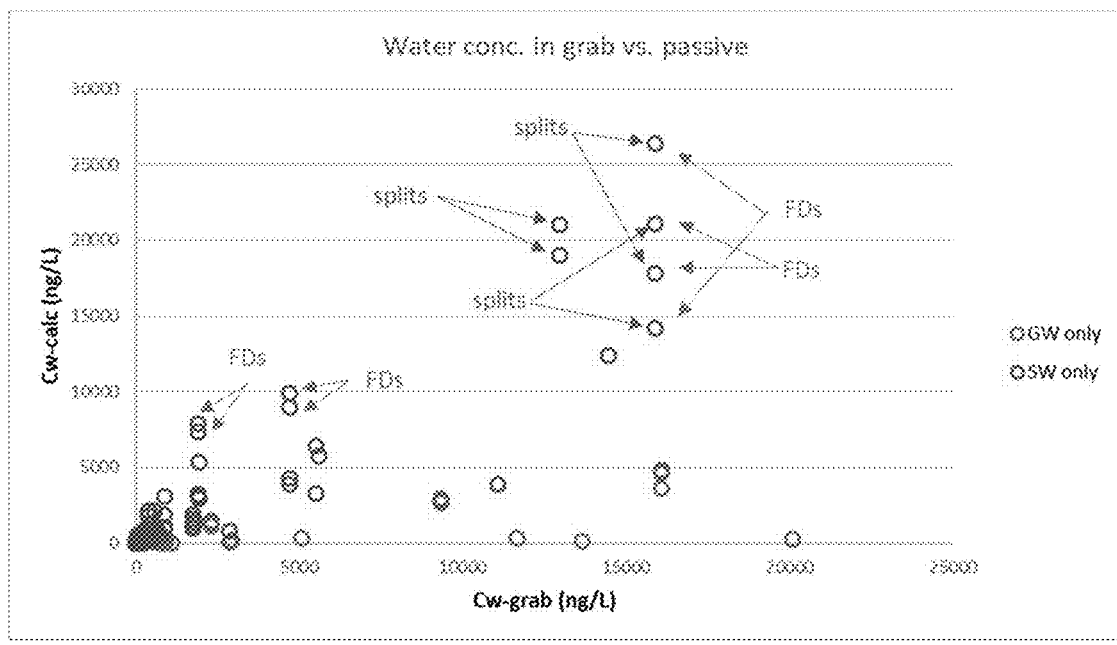
FIG. 23 shows calculated water concentrations (Cw-calc) derived from passive sampler results vs the average deployment and retrieval grab water sample concentrations (Cw-grab). In calculation of the above Cw-calc the $K_d$ was adjusted for the effect of organic carbon which caused an average decrease in log $K_d$ by 0.8 units. GW—groundwater samples, SW—surface water samples. FDs—field duplicate samplers, splits—two splits of sorbent cut out from one field sampler.

Overall a good agreement between the grab samples and passive sampler derived values was achieved in surface water samples but not in groundwater samples, where the passive sampler data were skewed low compared to water grab samples. It can be noticed that for certain Cw-grab values multiple Cw-calc values exist. These represent field duplicate (FD) samplers (two separate sampling devices deployed within one meter of each other) or splits of the same sampler created by sectioning the PUF from one sampler into two segments (bottom and top). The agreement between select FDs and splits is shown in FIG. 23. It can be seen that the agreement between the splits and FDs is very good in most cases with the exception of the highest concentration sampler where the discrepancy between both the FDs and the splits is somewhat elevated.

We discovered that groundwater monitoring well passive samplers can significantly under-represent the aqueous concentrations of PFAS.

Discussion and Summary of Field Data

While the data observed good agreement between passive sampler and grab water sample results, the two measurements are not directly comparable because: passive samplers measure time-integrated concentrations over the period of deployment while grab samples represent discrete point in time (in this case an average of two time points—deployment and retrieval day); and passive samplers typically only accumulate the freely dissolved fractions of contaminants whereas grab samples also include particle and colloid-bound contaminants. As such, passive sampler derived concentrations are almost always lower than that concentrations measured in bulk water samples. Nonetheless, the passive sampler performed well in surface water samples, with the passive sampler results representing on average 119% of the groundwater grab water sample results when matrix-influence partition coefficients were used in the calculation of PUF data. This highlights the importance of, first, investigating the influence of the matrix on the $K_d$ and then of collecting the necessary water quality and geochemical information (pH, ionic strength, organic carbon) to allow the necessary, site-specific adjustments to the $K_d$.

The passive sampler results for groundwater samples were significantly lower than the results of grab water sample analysis. First, it is well known that water temperature can affect partitioning of dissolved contaminants onto solids in aquatic systems. The impact of water temperature on PFAS partitioning to PUF ($K_d$) has not yet been investigated and therefore could not be corrected for. The groundwater temperatures were on the order of 16° C. whereas the surface water temperatures were about 25° C. which is the room temperature at which the $K_d$ values were experimentally determined in the laboratory, so the laboratory-derived $K_d$s were appropriate for the surface water samples but not as much for groundwater samples. For most environmental contaminants the decrease in temperature causes an increase in $K_d$; however, several studies suggest that the opposite may be true for PFAS, meaning that the $K_d$ decreases with decreasing temperature. Lower $K_d$ will result in higher calculated water concentrations (see Equation above) and therefore could explain why the passive sampler calculated results are lower than the concentrations measured in grab samples. Another possibility is that the dissolved PFAS exchange between the inside of the groundwater well and the rest of the aquifer was slower than the uptake of PFAS by the passive sampler, in which case the water in the well would become depleted in PFAS and therefore the uptake rate of PFAS by the passive sampler would be lower. That could cause for the passive sampler to not be fully equilibrated during the four-week deployment period, which would cause the passive sampler results to be lower than grab water samples obtained through active pumping. To address this problem, we have designed passive samplers that overcome the problem with PFAS depletion.

Figure 24:
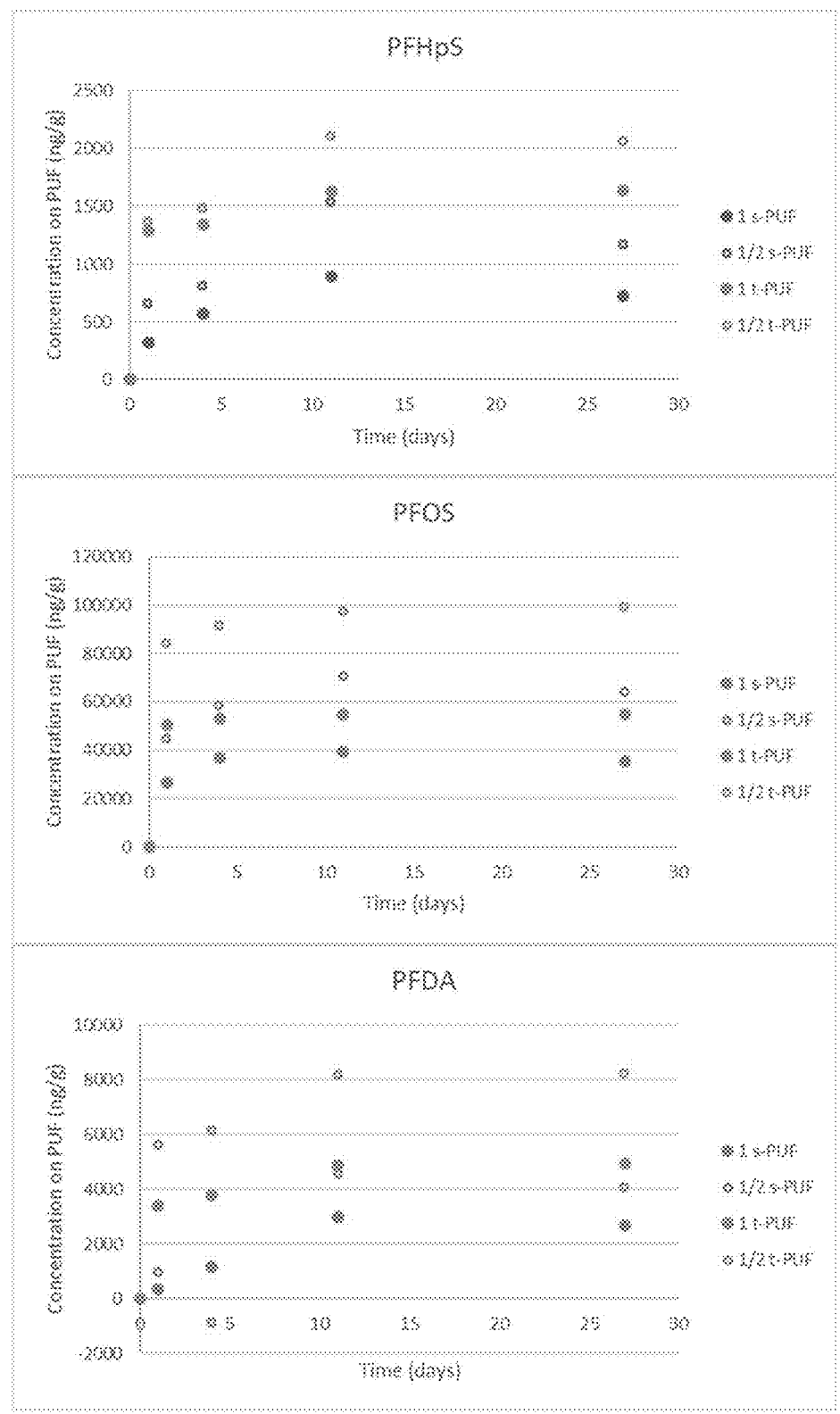
FIG. 24 shows the uptake of PFAS analytes by ether-based PUF (t-PUF) and ester-based PUF (s-PUF) in "full" size of 1×1 cm (data series starting in 1) or half the full size (data series starting in ½).

To investigate the effect of limited volume of water on the experimentally derived $K_d$ values, experiments of adsorption in batches of the same volume and concentration of PFAS but different size of PUF were conducted. Specifically, a series of bottles with 125 mL of PFAS solution in 0.01M NaCl as background electrolyte were prepared. A full PUF the size of approximately 1×1 cm was then added to three of the bottles, and a piece of half-sized PUF (about 1×0.5 cm) was added to another three bottles. The solutions were sampled at time zero (before adding PUF) and then again after 1, 4, 11, and 27 days. This experiment was conducted for both ether- and ester-based PUF (t-PUF and s-PUF, respectively). The results for select analytes are shown in the FIG. 24. While the two sized of PUF achieve equilibrium in about the same length of time, the equilibrium concentrations are different. The half-sized PUF accumulated about 30-50% more analytes on per gram basis than the full sized PUF. The same was true for both s-PUF and t-PUF. This shows that the limited volume of water used in the experimental setup limited the mass of analyte that adsorbed to PUF before it reached equilibrium with its surroundings. As such, the $K_d$ values derived in this manner are lower than they would be in an "infinite source" setting such as a large natural water body. Lower $K_d$ values result in elevated calculated water concentration for field samples. For higher accuracy, the $K_d$ coefficients need to be derived using an alternative method, for example a flow through tank to ensure the concentration of the analytes stays constant over time.

What is claimed is:

1. A PFAS groundwater sampler, comprising:
    a housing comprising a wall or walls that define an internal cross-sectional area;
    a PFAS sorbent material disposed within the housing;
    wherein the sampler has a mass of at least 0.05 grams and a ratio of sorbent mass to housing internal cross-sectional area of no more than 3 g/10 cm$^2$; and wherein the sorbent has a log $K_d$ of 10 or less for each of PFOA and PFOS and PFBS.

2. The sampler of claim 1 wherein the sorbent is a polymer.

3. A PFAS sampler, comprising:
    a PFAS sorbent film or foam that is covered by a copper mesh.

4. The PFAS sampler of claim 3 comprising five layers wherein the PFAS sorbent film or foam is sandwiched between two pieces of copper mesh and two pieces of stainless steel mesh such that the sampler comprises layers of the orders: stainless steel:copper:PFAS sorbent:copper: stainless steel.

5. The PFAS groundwater sampler of claim 1 wherein the sampler has a ratio of sorbent mass to housing internal cross-sectional area of no more than 1 g/10 cm$^2$.

6. The PFAS groundwater sampler of claim 1 wherein the sorbent is a polymeric foam.

7. A PFAS groundwater sampler, comprising:
    a housing comprising a wall or walls that define an internal cross-sectional area;
    a PFAS sorbent material disposed within the housing;
    wherein the sampler has a mass of at least 0.05 grams and a ratio of sorbent mass to housing internal cross-sectional area of no more than 3 g/10 cm$^2$; wherein the sorbent is a polymeric foam and wherein the foam comprises two types of polyurethane.

8. The PFAS groundwater sampler of claim 7 wherein the two types are ether-polyurethane and ester-polyurethane.

9. A PFAS groundwater sampler, comprising:
    a housing comprising a wall or walls that define an internal cross-sectional area;
    a PFAS sorbent material disposed within the housing;
    wherein the sampler has a mass of at least 0.05 grams and a ratio of sorbent mass to housing internal cross-sectional area of no more than 3 g/10 cm$^2$; wherein the sorbent is a polymeric foam and wherein the polymeric foam is further characterizable by at least one of the parameters shown in Table 2, 4, or 5 and having a value of ±50% of that parameter as shown in Table 2, 4, or 5.

10. The PFAS groundwater sampler of claim 6 wherein the sorbent is a single material.

* * * * *